US009066880B2

(12) United States Patent
Meyer et al.

(10) Patent No.: US 9,066,880 B2
(45) Date of Patent: Jun. 30, 2015

(54) USE OF DIHYDRODEHYDRODIISOEUGENOL AND PREPARATIONS COMPRISING DIHYDRODEHYDRODIISOEUGENOL

(75) Inventors: Imke Meyer, Bodenwerder (DE); Oskar Koch, Göttingen (DE); Jean Krutmann, Wegberg (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 13/639,646

(22) PCT Filed: Apr. 8, 2010

(86) PCT No.: PCT/EP2010/054667
§ 371 (c)(1),
(2), (4) Date: Dec. 20, 2012

(87) PCT Pub. No.: WO2010/070152
PCT Pub. Date: Jun. 24, 2010

(65) Prior Publication Data
US 2013/0101650 A1 Apr. 25, 2013

(51) Int. Cl.
*A61K 8/49* (2006.01)
*A61K 31/343* (2006.01)
*A61K 45/06* (2006.01)
*A61Q 90/00* (2009.01)
*A61Q 19/08* (2006.01)
*A61Q 1/10* (2006.01)
*A61Q 5/00* (2006.01)
*A61Q 5/02* (2006.01)
*A61Q 5/06* (2006.01)
*A61Q 5/12* (2006.01)
*A61Q 7/00* (2006.01)
*A61Q 17/04* (2006.01)

(52) U.S. Cl.
CPC ........... *A61K 8/4973* (2013.01); *A61K 2800/59* (2013.01); *A61K 2800/782* (2013.01); *A61K 2800/92* (2013.01); *A61Q 1/10* (2013.01); *A61Q 5/004* (2013.01); *A61Q 5/02* (2013.01); *A61Q 5/06* (2013.01); *A61Q 5/12* (2013.01); *A61Q 7/00* (2013.01); *A61Q 17/04* (2013.01); *A61Q 19/08* (2013.01); *A61K 31/343* (2013.01); *A61K 45/06* (2013.01)

(58) Field of Classification Search
CPC ... A61K 8/4973; A61K 31/343; A61K 45/06; A61K 2800/59; A61K 2800/782; A61Q 90/00
See application file for complete search history.

(56) References Cited

U.S. PATENT DOCUMENTS 4,304,785 A * 12/1981 Griengl et al. ............... 514/469
2006/0216251 A1 * 9/2006 Morariu ......................... 424/59

FOREIGN PATENT DOCUMENTS

| DE | 2812664 A1 | 9/1979 |
| EP | 0595297 A1 | 5/1994 |
| JP | S54138530 A | 10/1979 |
| JP | 2005306792 A | 11/2005 |
| WO | WO-2008156345 A2 | 12/2008 |

OTHER PUBLICATIONS

Takeyoshi et al., "Skin sensitization potency of isoeugenol and its dimers evaluated by a non-radioisotopic modification of the local lymph node assay and guinea pig maximization test" Journal of Applied Toxicology (2007), vol. 28, pp. 530-534.*
Lindgren et al., "Studies on Lignin Models" Acta Chemica Scandinavica (1954), vol. 8, pp. 954-960.*
Lee et al., "An intravenous formulation decision tree for discovery compound formulation development" International Journal of Pharmaceutics (2003), vol. 253, pp. 111-119.*
International Search Report with references cited and Written Opinion under Rule 43 PCT, attached to Search Report, PCT Application No. PCT/EP2010/054667.
Japanese Office Action, issued in parallel JP Application No. 2013-503008, dated May 22, 2014, together with Summary of the Japanese Office Action.

* cited by examiner

*Primary Examiner* — Abigail Fisher
*Assistant Examiner* — Daniel L Branson
(74) *Attorney, Agent, or Firm* — Novak Druce Connolly Bove + Quigg LLP

(57) ABSTRACT

This invention relates to cosmetic and pharmaceutical preparations comprising
(i) a diastereomer or a mixture of two or more diastereomers of the compound of formula (I)

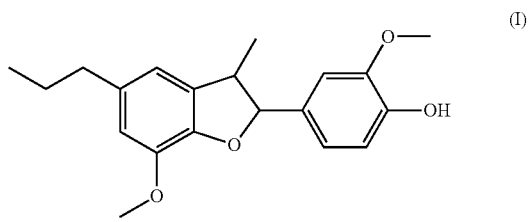

or
(ii) a salt of a diastereomer or of a mixture of two or more diastereomers of the compound of formula (I) or
(iii) a mixture of two or more salts of a diastereomer or of a mixture of two or more diastereomers of the compound of formula (I),
a diastereomer, salt or a mixture as defined above as a drug for topical application and/or for the treatment of lipoatrophy;
the non-therapeutic use of a diastereomer, salt or a mixture as defined above for the prevention, treatment or reduction of skin aging, especially skin wrinkles;
the use of a diastereomer, salt or a mixture as defined above for the production of an orally administered non-pharmaceutical preparation.

13 Claims, No Drawings

USE OF DIHYDRODEHYDRODIISOEUGENOL AND PREPARATIONS COMPRISING DIHYDRODEHYDRODIISOEUGENOL

RELATED APPLICATIONS

This application is a national stage application (under 35 U.S.C. §371) of PCT/EP2010/054667, filed Apr. 8, 2010, which is incorporated herein by reference in its entirety.

The present invention primarily relates to cosmetic and pharmaceutical preparations comprising
    (i) a diastereomer or a mixture of two or more diastereomers of the compound of formula (I)

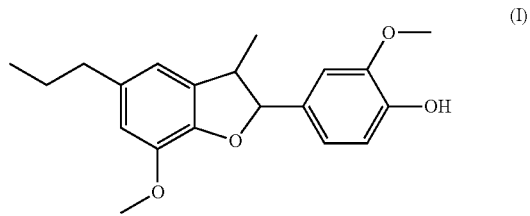 [SMILES: CCCc1cc(OC)c2c(c1)C(C)C(c1ccc(O)c(OC)c1)O2]

(2-Methoxy-4-(7-methoxy-3-methyl-5-propyl-2,3-dihydro-benzofuran-2-yl)-phenol, also known as dihydrodehydrodiisoeugenol);
or
    (ii) a salt of a diastereomer or of a mixture of two or more diastereomers of the compound of formula (I) or
    (iii) a mixture of two or more salts of a diastereomer or of a mixture of two or more diastereomers of the compound of formula (I),
a diastereomer, salt or a mixture as defined above as a drug for topical application and/or for the treatment of lipoatrophy;
the non-therapeutic use of a diastereomer, salt or a mixture as defined above for the prevention, treatment or reduction of skin aging, especially skin wrinkles; and/or the stimulation of the adipogenesis to increase the number of differentiated adipocytes and/or the inhibition of the lipolysis to alter the breakdown of stored lipids and thus increase the size of differentiated adipocytes, and/or the treatment of the subcutis to increase the lipid content in the human subcutaneous adipose tissue, and/or the inhibition of the formation of free radicals and breakdown of free radicals; and an appropriate non-therapeutic method;
the use of a diastereomer, salt or a mixture as defined above for the production of an orally administered non-pharmaceutical preparation.

Wrinkles in the skin can be attributed to various causes, with the different layers of the skin having different effects on the appearance of the skin. Most commonly the formation of skin wrinkles is prevented by influencing the cutis of the skin, consisting of the epidermis and dermis. However, the subcutis, also known as fat tissue or adipose tissue of the skin, plays a decisive part in the aging of the skin and the formation of skin wrinkles.

The adipose tissue in the body changes dramatically over lifetime. In this process the location of the adipose tissue has an influence on the changes in the tissue. So with increasing age the amount of fat in the subcutaneous adipose tissue decreases and conversely increases in the visceral adipose tissue. In particular in the face and neck the amount of fat in the adipose tissue reduces with age. The reduction in stored fat leads to a thinner subcutis. As a result of this the cutis is much less well padded, which is associated with the formation of visible skin wrinkles.

In the adipose tissue there is a sufficient number of precursor cells of fat cells, known as preadipocytes, which do not store any fat. Thus 15-50% of the cells of the adipose tissue are preadipocytes. In order to store fat these preadipocytes must go through the process of differentiation, which in relation to fat cells is known as adipogenesis. The differentiation of cells is generally the alteration of the regulation of the gene activity of a cell, so that by means of transcription and protein biosynthesis various proteins are created in the cells and cells can be distinguished according to appearance and function. Thus, only after differentiation adipocytes express enzymes which are necessary for the storage of fat. In the un-differentiated preadipocytes (the precursor cells) these enzymes are not expressed or only to a very small extent.

However in older skin the adipocytes differentiate from preadipocytes to a lesser extent than in younger skin. The reduced differentiation is attributable to a lower expression of so-called adipogenic transcription factors, which include by way of example peroxisome proliferator-activated receptor gamma (PPAR gamma) and CCAAT/enhancer binding protein alpha (C/EBP alpha).

In addition the content of tumor necrosis factor-alpha (TNF-alpha) has an influence on the amount of stored fat. More TNF-alpha is secreted from the adipose tissue of older skin. This increased secretion of TNF-alpha brings about by means of various mechanisms the reduction in the fat content of the adipose tissue, wherein the following mechanisms in particular have a decisive influence on the fat content:

(i) The adipogenesis/differentiation of preadipocytes is inhibited, wherein the TNF-alpha has an effect on the expression of various adipogenic and anti-adipogenic transcription factors. Apart from a lower number of differentiated adipocytes this mechanism results also in a lower content of stored lipids and thus a reduced size of the adipocytes compared with younger skin.

(ii) The lipolysis in the adipocytes, the process of hydrolysis of already stored triglycerides, is stimulated by TNF-alpha. The content of stored lipids and thus the size of the fat cells is reduced compared to younger skin.

These processes in the skin, which are attributable to natural aging or in younger skin can also be caused by illness, specific treatment methods or extrinsic factors, lead to a skin that appears thin, finely wrinkled and tired. This loss of subcutaneous adipose tissue is also referred to lipoatrophy or lipatrophy (Duden "Wörterbuch medizinische Fachausdrücke" [*Dictionary of Medical Terms*], 1979).

A known method of compensating for this deficit in subcutaneous adipose tissue is fat injection, also known as lipofilling, lipoaugmentation or lipotransfer. Here in most cases endogenous fat cells—taken from the abdominal or hip region—are injected into the subcutaneous tissue of, for example, the face. This method is expensive and in addition not very long-lasting, since the fat is decomposed by the endogenous enzymes. This decomposition happens more quickly with each successive injection so that renewed application after increasingly shorter periods becomes necessary. In addition, side effects such as inflammatory processes following application are known. Post-operative swellings for 1 or 2 weeks or visible irregularities can also occur.

The present invention is aimed on the prevention of the above-described mechanisms which lead to a loss of subcutaneous adipose tissue. Another aim of the invention is the enhancement of the quantity of lipids stored in the subcutis through an increased number and size of the differentiated adipocytes. In order to allow for effective prevention, treatment or reduction of skin aging, it is desirable that a cosmetic or pharmaceutical preparation achieves both of the following two effects:

(a) stimulation of adipogenesis to increase the number of differentiated adipocytes and
(b) inhibition of lipolysis to alter the breakdown of stored lipids and thus increase the size of differentiated adipocytes.

Cosmetic preparations to enhance the incorporation of lipids are already known. In US 2009/0253666 preparations comprising sarsasapogenin are disclosed which are said therein to enhance the incorporation of lipids in the subcutis. However, experiments have shown that sarsasapogenin, although stimulating the adipogenesis (above mentioned effect (a) has no effect on the lipolysis in differentiated adipocytes. Thus, differentiation of cells and incorporation of lipids is stimulated, but the breakdown of incorporated lipids (above mentioned effect (b)) which is stimulated in elderly skin by an elevated TNF-alpha level is not inhibited. So the success is limited when applying sarsasapogenin and preparations containing sarsasapogenin because the breakdown of lipids remains high.

US 2007/166255 provides preparations based on certain natural lignans for the treatment of topical discomforts and ailments including sunburn, radiation burn, thermal burn and blisters, diaper rash, shaving burn, wound, venous cannulation, acne, darkened skin pigmentation, skin wrinkles, dandruff, and hair loss. Unfortunately most of the natural lignans are UV degradable because of the presence a double bond.

WO 2007/001150 discloses a method for treating PPAR (peroxisome proliferator activated receptor)-mediated diseases, which comprises administering an effective amount of macelignan or a pharmaceutically acceptable salt thereof to a subject. Macelignan is a typical lignan-based compound which is found in *Myristica fragrans*. PPAR mainly controls expression of genes participating in fat metabolism or genes participating in differentiation of adipocytes.

WO 2008/156345 discloses the use of a lignin compound which is selected from the group consisting of fragrin A, austobailignan 7, licarin E and macelignan for preparing an agent for reducing wrinkles, induction of collagen synthesis or suppression of collagen decomposition. Licarin E comprises a propenyl group which might render this compound susceptible to UV-induced degradation.

Surprisingly it was found that the above objects, especially stimulation of adipogenesis and/or inhibition of lipolysis can be achieved by the compound of formula (I)

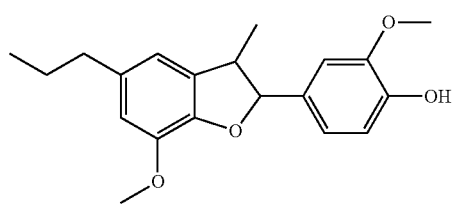

(I)

(2-Methoxy-4-(7-methoxy-3-methyl-5-propyl-2,3-dihydro-benzofuran-2-yl)-phenol, also known as dihydrodehydrodiisoeugenol)

the compound of formula (I) as a drug for topical application and/or for the treatment of lipoatrophy;

cosmetic or pharmaceutical preparations comprising the compound of the formula (I), the non-therapeutic use of the compound of formula (I) for the prevention, treatment or reduction of skin aging, especially skin wrinkles; and/or the stimulation of the adipogenesis to increase the number of differentiated adipocytes and/or the inhibition of the lipolysis to alter the breakdown of stored lipids and thus increase the size of differentiated adipocytes, and/or the treatment of the subcutis to increase the lipid content in the human subcutaneous adipose tissue, and/or the inhibition of the formation of free radicals and breakdown of free radicals; and an appropriate non-therapeutic method;

the use of the compound of formula (I) for the production of an orally administered non-pharmaceutical preparation.

References in the context of prior art to "the compound of formula (I)" or "the general compound of formula (I)" denote compositions consisting of unspecified diastereomers falling under formula (I) in an unknown ratio. With reference to the present invention, particularly the above list of 5 items, "the compound of formula (I)" means, unless explicitly stated otherwise, a) a diastereomer selected of the group consisting of the diastereomer of formula (Ia)

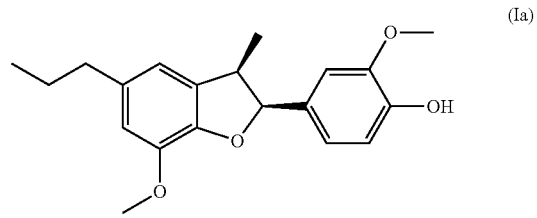 [SMILES: CCCc1cc(OC)c2c(c1)[C@@H](C)[C@@H](c1ccc(O)c(OC)c1)O2]

(Ia)

the diastereomer of formula (Ib)

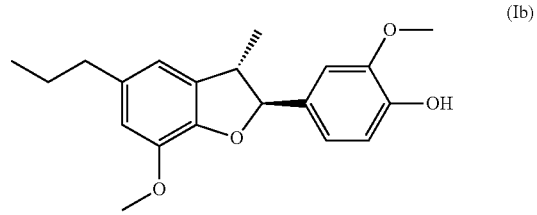 [SMILES: CCCc1cc(OC)c2c(c1)[C@H](C)[C@@H](c1ccc(O)c(OC)c1)O2]

(Ib)

the diastereomer of formula (Ic)

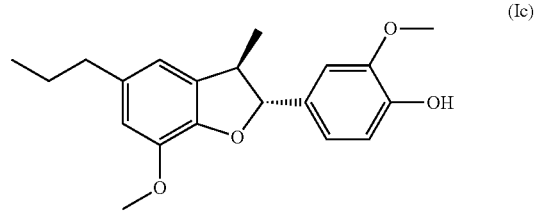 [SMILES: CCCc1cc(OC)c2c(c1)[C@@H](C)[C@H](c1ccc(O)c(OC)c1)O2]

(Ic)

and the diastereomer of formula (Id)

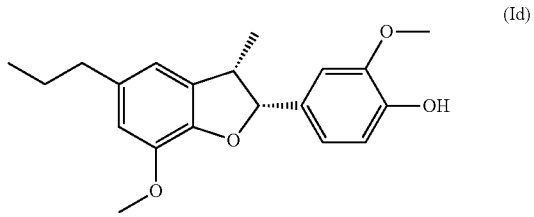 [SMILES: CCCc1cc(OC)c2c(c1)[C@H](C)[C@H](c1ccc(O)c(OC)c1)O2]

(Id)

b) a salt of a diastereomer of group a), preferably a cosmetically and/or pharmaceutically acceptable salt thereof,
c) a mixture of two or more salts of a diastereomer of group a), each salt preferably being cosmetically and/or pharmaceutically acceptable,
d) a mixture of two or more diastereomers of group a),
e) a salt of a mixture of two or more diastereomers of group a), preferably a cosmetically and/or pharmaceutically acceptable salt thereof, and/or
f) a mixture of two or more mixtures of group c) of different diastereomers.

Among above groups a)-f) the following items are preferred
the diastereomer of formula (Ib),
the diastereomer of formula (Ic),
a mixture of the diastereomer of the formula (Ib) and the diastereomer of the formula (Ic),
a salt of the diastereomer of formula (Ib),
a mixture of two or more salts of the diastereomer of formula (Ib),
a salt of the diastereomer of the formula (Ic),
a mixture of two or more salts of the diastereomer of formula (Ic),
a mixture of one or more salts of the diastereomer of the formula (Ib) and one or more salts of the diastereomer of the formula (Ic).

JP 2005306792 discloses benzofuran derivatives which are useful for skin lightening. These benzofuran derivatives are represented by a general formula which encompasses the general compound of formula (I) as defined above, but the general compound of formula (I) is not individually disclosed in JP 2005306792. Compared with most of the benzofuran derivatives listed in JP2005306792 the compound of formula (I) according to groups a), b), c), d), e) and/or f) has the advantage of a better UV-stability.

CA 22 98 677 describes benzofurans, which were isolated from an extract of *Aristolochia taliscana*, and derivatives of these natural benzofurans. The benzofuran derivatives described are inter alia used as anti-tumour agents, since a cytotoxic effect is attributed to them. These benzofuran derivatives are represented by a general formula which encompasses the general compound of formula (I) as described above, but the general compound of formula (I) is not individually disclosed in CA 22 98 677. Several benzofuran type compounds isolated from *Aristolochia taliscana* have a propenyl residue. Because of this residue the derivatives are unstable under UV irradiation and therefore have limited suitability as ingredients of cosmetic preparations.

The use of benzofuran derivatives as therapeutic agents (drugs) for the treatment of diseases of the liver is described in DE 28 12 664. 2,3-Dihydro-2-(4-hydroxy-3-methoxyphenyl)-7-methoxy-3-methyl-5-propenylbenzofuran (referred to as dehydrodiisoeugenol) and 2,3-Dihydro-3-(4-hydroxy-3-methoxyphenyl)-7-methoxy-3-methyl-5-propylbenzofuran (referred to as Dihydrodehydrodiisoeugenol) are among the preferred drugs described in DE 28 12 664. The preferred forms of administration are tablets, gelatin capsules or injectable solution. Topical application and treatment of the skin or lipoatrophy are not described.

Sarkanen et al. (Journal of Chem. Soc. Perkin Trans. I, (1973) 1869-1877) describe the synthesis of benzofuran derivatives including dihydrodehydrodiisoeugenol which is obtained by hydrogenation of a solution of 2,3-dihydro-2-(4-hydroxy-3-methoxyphenyl)-7-methoxy-trans-3-methyl-5-(Z)-propenylbenzofuran (100 mg) in absolute ethanol (20 ml) at 1 atm over 5% Pd—C (20 mg). After 30 min, filtration, evaporation, and crystallization from hexane dihydrodehydrodiisoeugenol was obtained. The same substance was obtained by catalytic hydrogenation of dehydrodiisoeugenol. The preparations comprising dihydrodehydrodiisoeugenol described by Sarkanen et al. are not encompassed by the cosmetic preparations of the present invention. Specifically, a preparation obtained or obtainable by catalytically hydrogenating 2,3-dihydro-2-(4-hydroxy-3-methoxyphenyl)-7-methoxy-trans-3-methyl-5-(Z)-propenyl-benzofuran or dehydrodiisoeugenol at 1 atm in absolute ethanol over 5% Pd—C (20 mg), a preparation consisting of the general compound of formula (I) and ethanol, a preparation consisting of the general compound of formula (I), ethanol and a catalyst consisting of palladium and carbon, and a preparation consisting of the general compound of formula (I) and hexane are excluded from the cosmetic preparations according to the present invention. Preferably, a cosmetic preparation according to the present invention is not a preparation comprising the general compound of formula (I) and at least one substance of the group consisting of ethanol, palladium, carbon, 3-dihydro-2-(4-hydroxy-3-methoxyphenyl)-7-methoxy-trans-3-methyl-5-(Z)-propenyl-benzofuran, dehydrodiisoeugenol, and hexane.

The synthesis of dihydrodehydrodiisoeugenol is further described by Aulin-Erdtmann (Svensk Kem. Tidskr. 54 (1942) 168). Dihydrodehydrodiisoeugenol is obtained by catalytically hydrogenating dehydrodiisoeugenol in alcohol in the presence of Pd—C wherein C is activated carbon obtained from animal blood and recrystallization of the hydrogenated substance from ligroin. The preparations comprising the general compound of formula (I) described by Aulin-Erdtmann are not encompassed by the cosmetic preparations of the present invention. More specifically a preparation obtained or obtainable by catalytically hydrogenating dehydrodiisoeugenol in alcohol in the presence of Pd—C wherein C is activated carbon obtained from animal blood, a preparation consisting of the general compound of formula (I), alcohol and a Pd—C catalyst wherein C is activated carbon obtained from animal blood, and a preparation consisting of the general compound of formula (I) and ligroin are excluded from the cosmetic preparations of the present invention. Preferably, a cosmetic preparation according to the present invention is not a preparation comprising the general compound of formula (I) and at least one substance of the group consisting of dehydrodiisoeugenol, alcohol, Pd—C (wherein C is activated carbon obtained from animal blood) and ligroin.

Bredenberg et al. (Holzforschung (1989), 43(2), 115-20) studied the thermal decomposition of dehydrodihydrodiisoeugenol at 603, 623, 648, 663 and 673 K. The experiments were performed in small boron silicate glass ampoules heated at the respective temperature for a time of 5 to 120 minutes. The preparations comprising the general compound of formula (I) described by Bredenburg et al. are not encompassed by the cosmetic preparations of the present invention. More specifically a preparation obtained or obtainable by thermolysis of the general compound of formula (I) at 603, 623, 648, 663 or 673 K and a preparation consisting of the general compound of formula (I) and compounds which are obtained or obtainable by thermolysis of the general compound of formula (I) at 603, 623, 648, 663 or 673 K are excluded from the cosmetic preparation of the present invention. Preferably a cosmetic preparation of the present convention does not comprise any compound which is obtained or obtainable by thermolysis of the general compound of formula (I) as described by Bredenburg et al.

Connors et al. (Holzforschung (1980), 34(1), 29-37) studied the hydrocracking of dihydrodehydrodiisoeugenol with tetralin as hydrogen donor at 400° C. A 15 minute hydrocracking of dihydrodehydrodiisoeugenol in tetralin at 400° C. produced approximately 12% monomeric phenols, of which the following were identified: guaiacol, catechol, phenol, 4-methylguaiacol, 4-methylcatechol, methylphenols, 4-propylguaiacol, 4-propylcatechol, propylphenols. The preparations comprising the general compound of formula (I) described by Connors et al. are not encompassed by the cosmetic preparations of the present invention. More specifically a preparation obtained or obtainable by hydrocracking of the general compound of formula (I) with tetralin at 400° C. and a preparation consisting of the general compound of formula (I) and guaiacol, catechol, phenol, 4-methylguaiacol, 4-methylcatechol, methylphenols, 4-propylguaiacol, 4-propylcatechol and propylphenols is excluded from the cosmetic preparations of the present invention. Preferably a cosmetic preparation of the present convention does not comprise any compounds which are obtained or obtainable by hydrocracking of the general compound of formula (I) with tetralin at 400° C. More preferably a cosmetic preparation of the present convention does not comprise a compound selected from the group consisting of guaiacol, catechol, phenol, 4-methylguaiacol, 4-methylcatechol, methylphenols, 4-propylguaiacol, 4-propylcatechol and propylphenols. Furthermore, preparations comprising the general compound of formula (I) and tetralin are no cosmetic preparations in the sense of the present invention. Tetralin has an irritant effect to the skin, the mucosa and the eyes. Therefore, preparations comprising tetralin are not suitable for cosmetic applications.

Gierer et al. (Acta Chemica Scandinavica (1973), 27(8), 2909-22) studied the enzymatic degradation of dihydrodehydrodiisoeugenol with peroxidase-hydrogen peroxide or laccase. Oxidation of dihydrodehydrodiisoeugenol with peroxidase/$H_2O_2$ was carried out as follows: Hydrogen peroxide (6 ml, 1%, 0.0017 mol) was added during 15 min to a stirred solution of dihydrodehydrodiisoeugenol (1.02 g, 0.00305 mol) in acetone (100 ml) and acetate buffer (130 ml) containing peroxidase (10 mg). The mixture was kept with stirring for 2 hours and then worked up by extraction with ethyl acetate. TLC of the residue (chloroform, developed five times) showed four components which were separated both as phenols and as acetates by chromatography on a silicic acid column (2×50 cm). The preparations comprising the general compound of formula (I) described by Gierer et al. are not encompassed by the cosmetic preparations of the present invention. More specifically a preparation obtained or obtainable by oxidizing the general compound of formula (I) with peroxidase/hydrogen peroxide wherein hydrogen peroxide (6 ml, 1%, 0.0017 mol) is added during 15 min to a stirred solution of the general compound of formula (I) (1.02 g, 0.00305 mol) in acetone (100 ml) and acetate buffer (130 ml) containing peroxidase (10 mg) is excluded from the cosmetic preparations of the present invention. A preparation obtained or obtainable by oxidizing the general compound of formula (I) with peroxidase/hydrogen peroxide wherein hydrogen peroxide (6 ml, 1%, 0.0017 mol) is added during 15 min to a stirred solution of the general compound of formula (I) (1.02 g, 0.00305 mol) in acetone (100 ml) and acetate buffer (130 ml) containing peroxidase (10 mg) and extraction with ethyl acetate is also excluded from the present invention. Furthermore a solution of the general compound of formula (I) (1.02 g, 0.00305 mol) and peroxidase (10 mg) in acetone (100 ml) and acetate buffer (130 ml) and a solution of the general compound of formula (I) (1.02 g, 0.00305 mol), acetate buffer (130 ml), peroxidase (10 mg) and hydrogen peroxide (6 ml, 1%, 0.0017 mol) in acetone (100 ml) are excluded from the cosmetic preparations of the present invention.

Preferably the cosmetic preparation of the present invention does not comprise any item selected from the group consisting of acetone, acetate buffer, hydrogen peroxide, peroxidase and ethyl acetate.

Furthermore, preparations comprising the general compound of formula (I) and chloroform are no cosmetic preparations in the sense of the present invention because chloroform is known to be harmful. Therefore, preparations comprising chloroform are not suitable for cosmetic applications.

Aoyama et al. (Journal of the Chinese Chemical Society (Taipei, Taiwan) (1991), 38(1), 77-84) studied the degradation of dihydrodehydrodiisoeugenol in organic solvents. Dihydrodehydrodiisoeugenol was prepared from dehydrodiisoeugenol by catalytic hydrogenation in EtOH-DMF in the presence of 5% Pd—C catalyst (1%) with shaking in an Adam's hydrogenation apparatus at room temperature under a hydrogen pressure of 30-40 psi for several hours. Dihydrodehydrodiisoeugenol was then treated in ethanol-water (1:1, v/v) in the presence of stannic chloride. The preparations comprising the general compound of formula (I) described by Aoyama et al. are not encompassed by the cosmetic preparations of the present invention. More specifically, preparations comprising the general compound of formula (I) and either DMF or stannic chloride are no cosmetic preparations in the sense of the present invention because DMF has an irritant effect on the skin, the mucosa and the eyes, and stannic chloride has a corrosive effect to the skin, the eyes and the mucosa. Therefore, preparations comprising DMF or stannic chloride are not suitable for cosmetic applications.

It appears that the prior art does not disclose the use of the compound of the formula (I) for the prevention, treatment or reduction of skin aging, in particular skin wrinkles, and thus the present invention pertains to
- the use of a compound of formula (I) of any group a) to f) for the prevention, treatment or reduction of skin aging, in particular skin wrinkles,
- cosmetic application of a compound of formula (I) of any group a) to f), and
- a compound of formula (I) of any group a) to f) as a drug for topical application and/or for the treatment of lipoatrophy.

Surprisingly it was found that
(i) a diastereomer or a mixture of two or more diastereomers of formula (I)

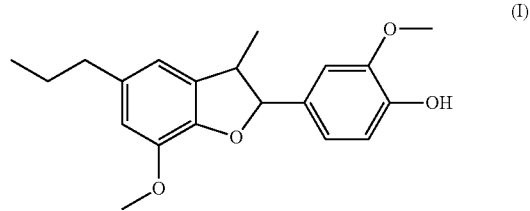 [SMILES: CCCc1cc(OC)c2c(c1)C(C)C(c1ccc(O)c(OC)c1)O2]

(I)

particularly a compound of formula (I) of group a) or d), or
(ii) a salt of a diastereomer or of a mixture of two or more diastereomers of formula (I), particularly a compound of formula (I) of group b) or e), or
(iii) a mixture of two or more salts of a diastereomer or of a mixture of two or more diastereomers of formula (I), particularly a compound of formula (I) of group c) or f) has a pronounced effect in the treatment of aging skin, discernible by means of ecographic determination of the subcutis layer thickness, in particular for preventing the reduced formation of fat deposits in the skin, in that the lipid content in the human subcutaneous adipose tissue is increased. The above compound of group (i), (ii) and/or (iii) is capable of influencing the subcutis with regard to the quantity of lipids stored, in that the lipid content in the human subcutaneous adipose tissue is increased.

Moreover, the above compound of group (i), (ii) and/or (iii) has a positive effect on skin irritation which can be associated with aging skin. Thus the activity of cyclooxygenase-2 (COX-2) is inhibited. COX-2 is an enzyme that plays an important role in the formation of prostaglandins, inflammatory mediators such as for example prostaglandin E2 (PGE2). Since increased PGE2 secretions from the cells of the skin lead to skin irritation, the activity of COX-2 has a decisive influence on skin irritation.

In addition, the above compound of group (i), (ii) and/or (iii) has a remarkable anti-oxidative capacity. The anti-oxidative capacity in elderly skin is reduced due to the decreased activity of the antioxidant defense enzymes. So the formation of reactive oxygen species (ROS) increases with aging. An above compound of group (i), (ii) and/or (iii), i.e.
(i) a diastereomer or a mixture of two or more diastereomers of formula (I)

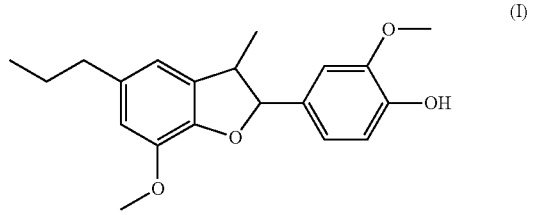 [SMILES: CCCc1cc(OC)c2c(c1)C(C)C(c1ccc(O)c(OC)c1)O2]

particularly a compound of formula (I) of group a) or d), or
(ii) a salt of a diastereomer or of a mixture of two or more diastereomers of formula (I), particularly a compound of formula (I) of group b) or e), or
(iii) a mixture of two or more salts of a diastereomer or of a mixture of two or more diastereomers of formula (I), particularly a compound of formula (I) of group c) or f) inhibits the formation of free radicals and breaks down free radicals and so results in an altered ROS formation in elderly skin.

A diastereomer or a mixture of two or more diastereomers of the compound of formula (I) may be used either in its neutral form or in the form of a salt or a mixture of two or more salts which are acceptable for the desired application. For cosmetic applications, cosmetically acceptable salts are preferred. For non-therapeutic oral applications orally acceptable salts are preferred. For pharmaceutical applications, pharmaceutically acceptable salts are preferred. Preferred cosmetically, orally or pharmaceutically acceptable salts of the compound of formula (I), i.e. one or more diastereomers (Ia) to (Id) are those in which the one or more counterions (counteracting cation) is selected from the group consisting of $Na^+$, $K^+$, $NH_4^+$, trialkylammonium $NHR^i_3{}^+$, $Ca^{2+}$, $Mg^{2+}$, $Zn^{2+}$ and $Al^{3+}$. In trialkylammonium $NHR^i_3{}^+$, preferably each $R^i$ independently of the other radicals $R^i$ denotes an alkyl group having 1 to 30 C-atoms, preferably having 4 to 22 C-atoms. Particularly preferred counterions are $Na^+$, $K^+$, $Ca^{2+}$ and/or $Mg^{2+}$.

An above compound of group (i), (ii) and/or (iii), i.e.
(i) a diastereomer or a mixture of two or more diastereomers of formula (I)

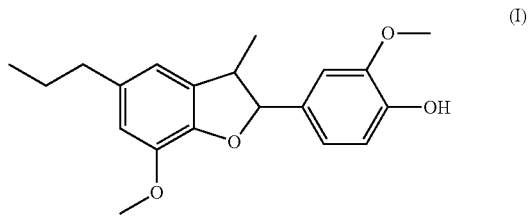 [SMILES: CCCc1cc(OC)c2c(c1)C(C)C(c1ccc(O)c(OC)c1)O2]

particularly a compound of formula (I) of group a) or d), or
(ii) a salt of a diastereomer or of a mixture of two or more diastereomers of formula (I), particularly a compound of formula (I) of group b) or e), or
(iii) a mixture of two or more salts of a diastereomer or of a mixture of two or more diastereomers of formula (I), particularly a compound of formula (I) of group c) or f) may be used either in a therapeutic or in a non-therapeutic manner. Thus the present invention relates to therapeutic aspects on the one hand and non-therapeutic, especially cosmetic aspects on the other hand.

In the context of the present application, a therapeutic or pharmaceutical preparation, use or method is considered as a preparation, use or method directed to a therapeutic (medical) treatment of the human or animal body, optionally with cosmetic (side) effects. The term "therapy" is understood to cover any treatment which is designed to cure, alleviate, remove or lessen the symptoms of, or prevent or reduce the possibility of contracting any disorder or malfunction of the human or animal body. The purpose of therapy is invariably to restore the organism from a pathological to its original condition, or to prevent pathology in the first place whereas a non-therapeutic improvement of performance takes as its starting point a normal state.

In its therapeutic aspects the present invention provides
(i) a diastereomer or a mixture of two or more diastereomers of formula (I)

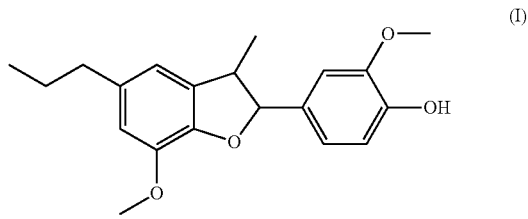 [SMILES: CCCc1cc(OC)c2c(c1)C(C)C(c1ccc(O)c(OC)c1)O2]

particularly a compound of formula (I) of group a) or d), or
(ii) a salt of a diastereomer or of a mixture of two or more diastereomers of formula (I), particularly a compound of formula (I) of group b) or e), or
(iii) a mixture of two or more salts of a diastereomer or of a mixture of two or more diastereomers of formula (I), particularly a compound of formula (I) of group c)

or f) as a drug for topical application and/or for the treatment of lipoatrophy; and a pharmaceutical preparation (also referred to as a pharmaceutical composition) comprising (i) a diastereomer or a mixture of two or more diastereomers of formula (I)

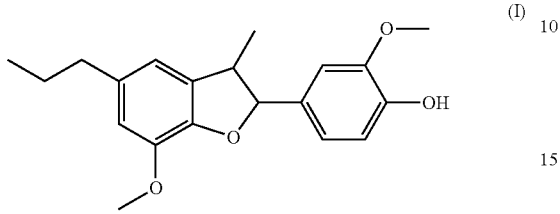

particularly a compound of formula (I) of group a) or d), or (ii) a salt of a diastereomer or of a mixture of two or more diastereomers of formula (I), particularly a compound of formula (I) of group b) or e), or (iii) a mixture of two or more salts of a diastereomer or of a mixture of two or more diastereomers of formula (I), particularly a compound of formula (I) of group c) or f) for topical application and/or for the treatment of lipoatrophy.

Another aspect of the present invention relates to non-therapeutic, especially cosmetic applications of an above compound of group (i), (ii) and/or (iii). In the context of the present invention, a non-therapeutic, e.g. cosmetic, use or method is free of any therapeutic (side) effects. Accordingly, a non-pharmaceutical, e.g. cosmetic preparation is a preparation which, when administered to a human or animal, is free of any therapeutic (side) effects.

In its non-therapeutic aspects the present invention primarily provides a cosmetic, especially a topical preparation (also referred to as a cosmetic, especially topic composition) comprising (i) a diastereomer or a mixture of two or more diastereomers of formula (I)

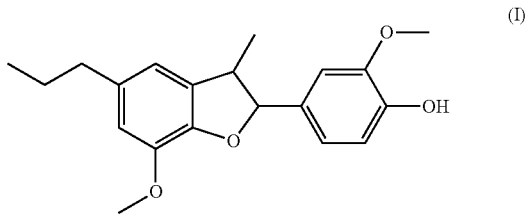 [SMILES: CCCc1cc(OC)c2c(c1)C(C)C(c1ccc(O)c(OC)c1)O2]

particularly a compound of formula (I) of group a) or d), or (ii) a salt of a diastereomer or of a mixture of two or more diastereomers of formula (I), particularly a compound of formula (I) of group b) or e), or (iii) a mixture of two or more salts of a diastereomer or of a mixture of two or more diastereomers of formula (I), particularly a compound of formula (I) of group c) or f) with the proviso that certain preparations which are explained hereinbelow are excluded, and the use of (i) a diastereomer or a mixture of two or more diastereomers of formula (I)

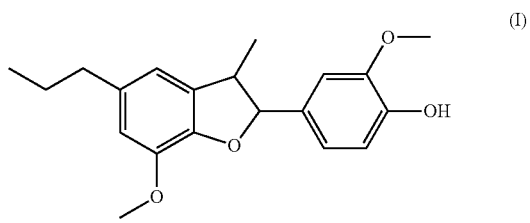

particularly a compound of formula (I) of group a) or d), or (ii) a salt of a diastereomer or of a mixture of two or more diastereomers of formula (I), particularly a compound of formula (I) of group b) or e), or (iii) a mixture of two or more salts of a diastereomer or of a mixture of two or more diastereomers of formula (I), particularly a compound of formula (I) of group c) or f) for the production of an orally administerable non-pharmaceutical preparation.

In the context of the present application the term "cosmetics" is understood to comprise any treatment of the skin, the appendages associated with the skin (e.g. hair, nails, glands) and the perceivable mucous membranes for the purpose of purification, care (preservative, prophylactic, or ameliorative), improvement of the appearance, decoration, coloration and improvement of the odor. Due to the application of cosmetic preparations directly on the skin or the mucous membranes or in the close vicinity of the skin, the mucous membranes or the eyes, substances which have an irritant or corrosive effect on the skin, the mucous membranes or the eyes are not suitable as components of cosmetic preparations. Accordingly the cosmetic preparations of the present invention do not contain substances which are classified by law as having an irritant or corrosive effect on the skin, the mucous membranes or the eyes. Furthermore the cosmetic preparations of the present invention do not comprise harmful substances in an amount which renders the total cosmetic preparation a harmful substance. Preferably the cosmetic preparations of the present invention do not comprise harmful substances at all.

The cosmetic, especially topical preparations according to the present invention are preferably used for topical treatment of the skin, preferably but not exclusively on the cheeks and/or on the temples and/or in the area of the nasolabial fold and/or on the neck and/or on the lips and/or on the eyelids and/or on the hands and/or in the area of the chest and/or on the arms.

The preparations listed hereinbelow are excluded from the cosmetic, especially topical, preparation of the present invention:

a preparation obtained or obtainable by catalytically hydrogenating dehydrodiisoeugenol in alcohol in the presence of Pd—C wherein C is activated carbon obtained from animal blood, a preparation consisting of the compound of formula (I), alcohol and a Pd—C catalyst wherein C is activated carbon obtained from animal blood, a preparation consisting of the compound of formula (I) and ligroin a preparation obtained or obtainable by catalytically hydrogenating 2,3-dihydro-2-(4-hydroxy-3-methoxyphenyl)-7-methoxy-trans-3-methyl-5-(Z)-propenyl-benzofuran or dehydrodiisoeugenol at 1 atm in absolute ethanol over 5% Pd—C (20 mg), a preparation consisting of the compound of formula (I) and ethanol, a preparation consisting of the compound of formula (I), ethanol and a catalyst consisting of palladium and carbon, a preparation consisting of the compound of formula (I) and hexane, a preparation obtained or obtainable by thermolysis of the compound of formula (I) at 603, 623, 648, 663 or 673 K, a preparation consisting of the compound of formula (I) and compounds which are obtained or obtainable by thermolysis of the compound of formula (I) at 603, 623, 648, 663 or 673 K, a preparation obtained or obtainable by hydrocracking of the compound of formula (I) with tetralin at 400° C., a preparation consisting of the compound of formula (I) and guaiacol, catechol, phenol, 4-methylguaiacol, 4-methylcatechol, methylphenols, 4-propylguaiacol, 4-propylcatechol and propylphenols, a preparation obtained or obtainable by oxidizing the compound of formula (I) with peroxidase/hydrogen peroxide wherein hydrogen peroxide (6 ml, 1%, 0.0017 mol) is added during 15 min to a stirred solution of the compound of formula (I) 1.02 g, 0.00305 mol) in acetone (100 ml) and acetate buffer (130 ml) containing peroxidase (10 mg)

a preparation obtained or obtainable by oxidizing the compound of formula (I) with peroxidase/hydrogen peroxide wherein hydrogen peroxide (6 ml, 1%, 0.0017 mol) is added during 15 min to a stirred solution of the compound of formula (I) (1.02 g, 0.00305 mol) in acetone (100 ml) and acetate buffer (130 ml) containing peroxidase (10 mg) and extraction with ethyl acetate a solution of the compound of formula (I) (1.02 g, 0.00305 mol) and peroxidase (10 mg) in acetone (100 ml) and acetate buffer (130 ml)

a solution of the compound of formula (I) (1.02 g, 0.00305 mol), acetate buffer (130 ml), peroxidase (10 mg) and hydrogen peroxide (6 ml, 1%, 0.0017 mol) in acetone (100 ml).

Preferably the cosmetic preparation according to the present invention is not a preparation as listed hereinbelow:

a preparation comprising the compound of formula (I) and at least one substance of the group consisting of ethanol, palladium, carbon, 2,3-dihydro-2-(4-hydroxy-3-methoxyphenyl)-7-methoxy-trans-3-methyl-5-(Z)-propenyl-benzofuran, and hexane, a preparation comprising the compound of formula (I) and at least one substance of the group consisting of alcohol, Pd—C (wherein C is activated carbon obtained from animal blood) and ligroin, a preparation comprising the compound of formula (I) and at least one compound which is obtained or obtainable by thermolysis of the compound of formula (I) at 603, 632, 648, 663 or 673 K, a preparation comprising the compound of formula (I) and at least one compound selected from the group consisting of guaiacol, catechol, phenol, 4-methylguaiacol, 4-methylcatechol, methylphenols, 4-propylguaiacol, 4-propylcatechol and propylphenols, a preparation comprising the compound of formula (I) and at least one item selected from the group consisting of acetone, acetate buffer, hydrogen peroxide, peroxidase, ethyl acetate, preparations comprising the compound of formula (I) and dehydrodiisoeugenol wherein the ratio of the amount of the compound of formula (I) to the amount of dehydrodiisoeugenol is below 5000:1 mol/mol.

Preferably, in the preparations according to the present invention the ratio of the amount of the compound of formula (I) to the amount of dehydrodiisoeugenol is at least 10000:1 mol/mol, further preferably at least 50000:1.

In the context of the above lists of excluded preparation any reference to "the compound of the formula (I)" includes all diaestereomers (Ia) to (Id) and salts thereof.

A pharmaceutical or cosmetic, especially topical preparation according to the present invention preferably comprises an effective amount of (i) a diastereomer or a mixture of two or more diastereomers of formula (I)

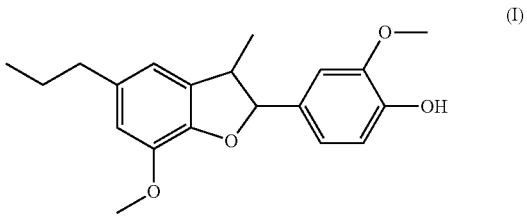 [SMILES: CCCc1cc(OC)c2c(c1)C(C)C(c1ccc(O)c(OC)c1)O2]

particularly a compound of formula (I) of group a) or d), or (ii) a salt of a diastereomer or of a mixture of two or more diastereomers of formula (I), particularly a compound of formula (I) of group b) or e), or (iii) a mixture of two or more salts of a diastereomer or of a mixture of two or more diastereomers of formula (I), particularly a compound of formula (I) of group c) or f) to
stimulate adipogenesis to increase the number of differentiated adipocytes and/or
inhibit lipolysis to alter the breakdown of stored lipids and thus increase the size of differentiated adipocytes, and/or
influence the subcutis with regard to the quantity of lipids stored, in that the lipid content in the human subcutaneous adipose tissue is increased, and/or
inhibit the formation of free radicals and/or to break down free radicals.

Preferably a pharmaceutical or cosmetic, especially topical preparation according to the present invention comprises an effective amount of (i) a diastereomer or a mixture of two or more diastereomers of formula (I)

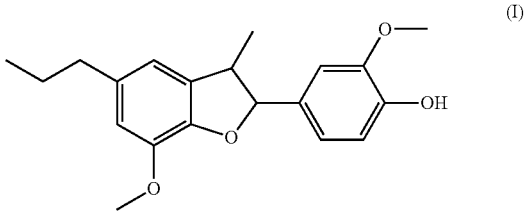

particularly a compound of formula (I) of group a) or d), or (ii) a salt of a diastereomer or of a mixture of two or more diastereomers of formula (I), particularly a compound of formula (I) of group b) or e), or (iii) a mixture of two or more salts of a diastereomer or of a mixture of two or more diastereomers of formula (I), particularly a compound of formula (I) of group c) or f) to stimulate adipogenesis to increase the number of differentiated adipocytes and
inhibit lipolysis to alter the breakdown of stored lipids and thus increase the size of differentiated adipocytes.

More specifically, a pharmaceutical and/or cosmetic, especially topical preparation according to the present invention comprises
(i) a diastereomer or a mixture of two or more diastereomers of formula (I)

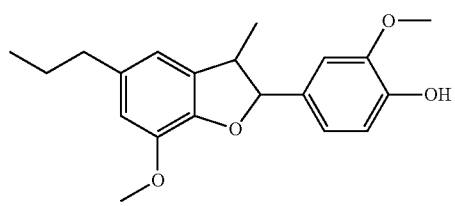

particularly a compound of formula (I) of group a) or d), or
(ii) a salt of a diastereomer or of a mixture of two or more diastereomers of formula (I), particularly a compound of formula (I) of group b) or e), or
(iii) a mixture of two or more salts of a diastereomer or of a mixture of two or more diastereomers of formula (I), particularly a compound of formula (I) of group c) or f)
without taking into account possible counterions in a total quantity of 0.001-5.0% by weight, preferably 0.005-2.0% by weight, and particularly preferably 0.01-1.0% by weight, and most preferably 0.02-0.50% by weight in relation to the total weight of the pharmaceutical or cosmetic, especially topical preparation.

In these concentrations an above compound of group (i), (ii) and/or (iii) can be incorporated well into common pharmaceutical or cosmetic, especially topical formulations such as pump sprays, aerosol sprays, creams, ointments, tinctures, lotions and the like. Thus, the pharmaceutical or cosmetic, especially topical, preparation according to the present invention preferably is a preparation selected from the group consisting of pump sprays, aerosol sprays, creams, ointments, tinctures, lotions.

Preferably, the pharmaceutical or cosmetic, especially topical, preparation according to the present invention is an aqueous preparation having a pH value in the range of from 5 to 9.

Moreover, the pharmaceutical or cosmetic, especially topical, preparation according to the present invention may be available in encapsulated form.

In addition to above compound of group (i), (ii) and/or (iii) the pharmaceutical or cosmetic, especially topical preparation according to the present invention may comprise one or more or all of the following ingredients
one or more substances that inhibit the matrix metalloproteinases (MMPs),
one or more substances which promote the formation of collagen in the tissue,
one or more preservatives,
one or more hair growth modulating agents,
one or more pharmaceutical and/or cosmetic carrier materials,
one or more substances with a physiological cooling effect,
one or more substances which cause a hot, sharp, tingly or prickly feeling on the skin or on the mucous membranes,
one or more substances which reduce the hypersensitivity of skin nerves,
one or more UV-A and/or UV-B filters,
one or more anti-irritants,
one or more hair care agents,
one or more anti-dandruff active ingredients,
one or more plant extracts which can be used for cosmetic or pharmaceutical purposes,
one or more surfactants,
one or more insect repellants.

Preferably a pharmaceutical or cosmetic, especially topical preparation according to the present invention comprises a combination of an above compound of group (i), (ii) and/or (iii) and one or more substances that inhibit the matrix metalloproteinases (MMPs).

Further preferably, a pharmaceutical and/or cosmetic, especially topical preparation according to the present invention comprises a combination of an above compound of group (i), (ii) and/or (iii) and one or more substances which promote the formation of collagen in the tissue.

A particularly preferable pharmaceutical or cosmetic, especially topical preparation according to the present invention comprises a combination of an above compound of group (i), (ii) and/or (iii) and one or more substances that inhibit the matrix metalloproteinases (MMPs) and one or more substances which promote the formation of collagen in the tissue.

Since skin aging, apart from reduced storage of fat in the adipose tissue, is also associated with a breakdown of the connective tissue, preferred pharmaceutical or cosmetic, especially topical preparations according to the invention contain substances which prevent a breakdown of the connective tissue. Here substances that inhibit the matrix metalloproteinases (MMPs) are advantageous. These enzymes are able to proteolytically break down macromolecules of the extracellular matrix (ECM) of the connective tissue, including the collagens. In particular the matrix metalloproteinase-1 (MMP-1), matrix metalloproteinase-2 (MMP-2) and matrix metalloproteinase-9 (MMP-9) are responsible for the breakdown of the connective tissue of the skin. Inhibition of MMPs is for example possible by the addition of ursolic acid, retinyl palmitate, propyl gallate, precocene, 6-hydroxy-7-methoxy-2,2-dimethyl-1(2H)-benzopyran, 3,4-dihydro-6-hydroxy-7-methoxy-2,2-dimethyl-1(2H)-benzopyran. The addition of peptides, which inhibit MMPs, to pharmaceutical or cosmetic, especially topical, preparations according to the present invention is also advantageous for inhibiting MMPs. Proteins or glycoproteins of soy and hydrolysed proteins from rice, peas or lupines inhibit MMPs and are thus a suitable additive. A combination with a plant extract, which inhibits MMPs, is likewise advantageous. Here mention can be made, for example, of an extract of Shiitake mushrooms. Also advantageous is the combination with extracts from the leaves of the Rosaceae family, Rosoideae subfamily. The use of blackberry leaf extract is of quite particular advantage, in particular as described in WO 2005/123101 A1.

In connection with the present invention, MMP-inhibitors to be used, preferably in combination, are retinyl palmitate, propyl gallate, precocene, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmaleimide and epsilon-amino-n-caproic acid, the serine protease inhibitor: phenylmethylsulphonyl fluoride, Collhibin (from Pentapharm; INCI: Hydrolyzed Rice Protein), Oenotherol (from Soliance; INCI: Propylene Glycol, Aqua, *Oenothera biennis* root extract, ellagic acid and ellagitannins, e.g. from pomegranate), phosphoramidon hinokitiol, EDTA, Galardin, EquiStat (from Collaborative Group; apple fruit extract, soy seed extract: ursolic acid, soy isoflavins & soy proteins), sage extracts, MDI (from Atrium; INCI: glycosaminoglycans), Fermiskin (from Silab/Mawi; INCI: water and *Lentinus Edodes* Extract), Actimp 1.9.3. (from Expanscience/Rahn; INCI: Hydrolyzed Lupine Protein), Lipobelle soy glycone (from Mibelle; INCI: alcohol, polysorbate 80, lecithin and soy isoflavones), extracts of green and black tea and numerous further plant extracts which are listed in WO 02/069992 (see tables 1-12 thereof).

In order to counter the breakdown of the connective tissue, preferred pharmaceutical or cosmetic, especially topic preparations according to the present invention comprise substances which promote the formation of collagen in the tissue is advantageous. Substances that are frequently used to increase collagen synthesis are for example substances such as ascorbic acid and derivatives thereof, retinol and derivatives of retinol or plant extracts such as for example *Aloe* and *Centella* species. Other substances which are suitable for boosting collagen synthesis include peptide substances and derivatives thereof such as e.g. carnitine, carnosine, creatine, matrikine peptides (e.g. lysyl-threonyl-threonyl-lysyl-serine) and further peptide structures such as palmitoylated pentapeptides (e.g. Matrixyl from Sederma) or the oligopeptide with the trade name Vincipeptide (from Vincience, France). Moreover, compounds such as asiatic acid, madecassic acid, madecassoside, asiaticoside, extracts of *Centella asiatica*, niacinamide, astaxanthine, glucans e.g. from yeasts and oats, soy extracts and soy isoflavones, such as genistein and daidzein, rutin, chrysin, morin, betel nut alkaloids, forskolin, betulinic acid, extracts of *Plantago* species, TGF-beta, extracts of *Ginkgo biloba*, glutamine and glycolic acid are used as collagen synthesis stimulators. Particular preference here is for the addition of a combination of *Aloe vera* extract, raspberry leaf extract and magnesium ascorbyl phosphate.

Moreover in addition to an above compound of group (i), (ii) and/or (iii) and—if available—the optional ingredients listed above the pharmaceutical or cosmetic, especially topical preparation according to the present invention may comprise one, more or all of the following ingredients:

preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, further anti-cellulite agents, in particular those described in WO 2007/077541, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO 2008/46676, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, skin warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO 2008/046676, virucides, abrasives, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO 2008/046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, and electrolytes.

A preferred pharmaceutical or cosmetic, especially topical, preparation of the present invention comprises a combination of the above compound of group (i), (ii) and/or (iii) with one or more hair growth modulating agents. Agents to stimulate hair growth are for example pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, microalgae or plants and plant parts of for example the genera dandelion (*Leontodon* or *Taraxacum*), *Orthosiphon*, *Vitex*, *Coffea*, *Paullinia*, *Theobroma*, *Asiasarum*, *Cucurbita* or *Styphnolobium*, *Serenoa repens* (saw palmetto), *Sophora flavescens*, *Pygeum africanum*, *Panicum miliaceum*, *Cimicifuga racemosa*, *Glycine max*, *Eugenia caryophyllata*, *Cotinus coggygria*, *Hibiscus rosa-sinensis*, *Camellia sinensis*, *Ilex paraguariensis*, licorice, grape, apple, barley or hops or/and hydrolysates from rice or wheat.

Agents to inhibit hair growth are for example activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, microalgae or plants and plant parts of for example the families Leguminosae, Solanaceae, Graminae, Asclepiadaceae or Cucurbitaceae, the genera *Chondrus*, *Gloiopeltis*, *Ceramium*, *Durvillea*, *Glycine max*, *Sanguisorba officinalis*, *Calendula officinalis*, *Hamamelis virginiana*, *Arnica montana*, *Salix alba*, *Hypericum perforatum* or *Gymnema sylvestre*.

Preferred pharmaceutical or cosmetics carrier materials, which may be a component of a pharmaceutical or cosmetic, especially topical preparation according to the invention, are solid or liquid at 25° C. and 1013 mbar (including highly viscous substances).

Preferred liquid carrier substances, which may be a component of a pharmaceutical or cosmetic, especially topical preparation according to the invention are selected from the group consisting of glycerol, 1,2-propylene glycol, 1,2-butylene glycol, 1,3-butylene glycol, 1,2-pentandiol, 1,2-hexandiol, 1,2-octandiol, 1,2-decandiol, ethanol, water and mixtures of two or more of said liquid carrier materials with water. Optionally, the pharmaceutical or cosmetic, especially topical preparations according to the invention may be produced using preservatives, solubilizers or antioxidants.

Preferred solid carrier materials, which may be a component of a pharmaceutical or cosmetic, especially topical, preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

Furthermore, the pharmaceutical or cosmetic, especially topical preparation according to the invention may be present in encapsulated form, these preferably being encapsulated with a solid covering material, which is preferably selected from starches, degraded or chemically or physically modified starches (in particular dextrins and maltodexterins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize, wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the covering of which dissolves very rapidly in the mouth or bursts when chewing. Production may take place, for example, as described in EP 0 389 700, U.S. Pat. Nos. 4,251,195, 6,214,376, WO 03/055587 or WO 2004/050069.

Furthermore, the pharmaceutical or cosmetic, especially topical preparation according to the invention may comprise one or more substances with a physiological cooling effect. Substances with a physiological cooling effect, which can be used as a component in a pharmaceutical or cosmetic, especially topical preparation according to the invention, are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (l-menthoxy)-2-methyl-1,2-propandiol, 1-menthyl-methyl-ether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or Na-(menthanecarbonyl)glycmethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(−)-isopulegol, 1-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), carboxamide (for example N-(2-(Pyridin-2-yl)ethyl)-3-p-menthancarboxamide or related compounds), oxamates as described in EP 2 033 688 A2.

Furthermore, the pharmaceutical or cosmetic, especially topical preparation according to the invention may comprise one or more substances which cause a hot, sharp, tingly or prickly feeling on the skin or on the mucous membranes. Suitable substances which cause a hot, sharp, tingly or prickly feeling on the skin or on the mucous membranes, in particular flavours with a heat-producing effect and/or sharp tasting compounds (sharp substances, are mentioned in WO 2005/123101.

Further, combinations with compounds which reduce the hypersensitivity of skin nerves based on their action as TRPV1 antagonists, e.g. Trans-t-Butylcyclohexanol, or indirect modulators of TRPV1 by an activation of u receptor, e.g. Acetyl tetrapeptide-15, are preferred.

In pharmaceutical or cosmetic, especially topical preparations according to the invention, the compound of formula (I), a pharmaceutically and/or cosmetically acceptable salt thereof or a mixture of two or more pharmaceutically and/or cosmetically acceptable salts is particularly advantageously combined with substances which absorb or reflect UV radiation, especially for cosmetic or skin-protecting purposes (in other words not for oral hygiene purposes), the total quantity of the filter substances being from 0.01% by weight to 40% by weight, preferably 0.1% to 10% by weight, in particular 1.0 to 5.0% by weight based on the total weight of the preparations, in order to provide pharmaceutical or cosmetic, especially topical preparations, which protect the hair or the skin from ultraviolet radiation. These preparations advantageously contain at least one UVA filter and/or at least one UVB filter and/or at least one inorganic pigment, so a light protection factor of at least >2 (preferably >5) is achieved. These preparations according to the invention may in this case be present in various forms such as, for example, are conventionally used for sun protection. They may thus be, for example, a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

Advantageous UV filters and inorganic light protection pigments are mentioned in WO 2005/123101. UV absorbers particularly suitable for combination are also mentioned in WO 2005/123101.

Advantageous inorganic light protection pigments are finely dispersed metal oxides and metal salts which are also mentioned in WO 2005/123101. The total quantity of inorganic pigments, in particular hydrophobic inorganic micropigments in the finished pharmaceutical or cosmetic, especially topical preparations of the present invention is advantageously from 0.1 to 30% by weight, preferably 0.5 to 10.0% by weight, based on the total weight of the preparations.

A combination of the compound of formula (I), a pharmaceutically and/or cosmetically acceptable salt thereof or a mixture of two or more pharmaceutically and/or cosmetically acceptable salts is particularly advantageously the (metal)-chelating agents may also be advantageous in some of the pharmaceutical or cosmetic, especially topical, preparations according to the invention. (Metal)-chelating agents to be preferably used are the compounds mentioned in WO 2005/123101.

Furthermore, it is advantageous to combine in a pharmaceutical or cosmetic, especially topical, preparation according to the invention the compound of formula (I) or a pharmaceutically and/or cosmetically acceptable salt thereof or a mixture of two or more pharmaceutically and/or cosmetically acceptable salts of the compound of formula (I) with ingredients which penetrate into the skin and protect the skin cells from inside against sun light-induced damage such as skin aging, skin inflammation and skin cancer. Respective ingredients, so called arylhydrocarbon receptor antagonists, are described in WO2007/128723. Preferred is 2-Benzylidene-5,6-dimethoxy-3,3-dimethylindan-1-one.

Pharmaceutical or cosmetic, especially topical preparations preferred according to the invention can also contain anti-inflammatory and/or redness and/or itch ameliorating ingredients. The compounds mentioned in WO 2005/123101 are advantageously used as anti-inflammatory or redness and/or itch ameliorating ingredients.

The quantity of anti-irritants (one or more compounds) in the pharmaceutical or cosmetic, especially topical preparations according to the invention is preferably 0.0001 to 20% by weight, particularly preferably 0.0001-10% by weight, in particular 0.001-5% by weight based on the total weight of the preparation.

The compound of formula (I) or a pharmaceutically and/or cosmetically acceptable salt thereof or a mixture of two or more pharmaceutically and/or cosmetically acceptable salts of the compound of formula (I) may advantageously be used, in particular, in pharmaceutical or cosmetic especially topical preparations in combination with insect repellents such as, for example, DEET, IR 3225, dragorepel (Symrise GmbH & Co. KG).

The compound of formula (I) or a pharmaceutically and/or cosmetically acceptable salt thereof or a mixture of two or more pharmaceutically and/or cosmetically acceptable salts of the compound of formula (I) can advantageously be used in particular in pharmaceutically or cosmetic, especially topical preparations in combination with hair care agents and anti-dandruff ingredients (for example climbazole, ketoconazole, piroctone oleamine, zinc-pyrithione).

The compound of formula (I) or a pharmaceutical and/or cosmetically acceptable salt thereof or a mixture of two or more pharmaceutically and/or cosmetically acceptable salts of the compound of formula (I) can also advantageously be used in numerous cases in combination with one or more preservatives in preparations according to the invention. The preservatives mentioned in WO 2005/123101 are preferably selected here.

Pharmaceutical or cosmetic, especially topical preparations according to the present invention may contain plant extracts which can be used for cosmetic or pharmaceutical purposes. The plant extracts which can be used for cosmetic purposes are preferably selected from the table of listed substances beginning on page 44 of the third edition of the handbook on the contents declaration of cosmetic agents, published by the Industrieverband Körperpflegemittel and Waschmittel e.V. (IKW), Frankfurt. The extracts mentioned in WO 2005/123101 are also particularly advantageous.

Moreover, pharmaceutical or cosmetic, especially topical preparations of the present invention may, in particular if crystalline or microcrystalline solid bodies such as, for example, inorganic micropigments are to be incorporated in the preparations, may also contain anionic, cationic, nonionic and/or amphoteric surfactants mentioned in WO 2005/123101.

The surfactant may be present in a concentration between 1 and 98% by weight, based on the total weight of the preparation of the present invention.

The oil phase of the pharmaceutical or cosmetic, especially topical preparations according to the present invention may advantageously be selected from the substance groups mentioned in WO 2005/123101.

Important areas of application of the pharmaceutical or cosmetic, especially topical preparations according to the invention are the protection of the skin and/or the hair against light, especially UV-light, treatment, care and cleaning of the skin and/or hair and decorative cosmetics, especially make-up. Accordingly, preparations according to the invention, depending on their structure, can be used, for example, as day protection cream, day or night cream, eye cream, sun protection or after-sun lotion, nourishing cream, a care mask, gel pads, facial tonic, moist care and cleaning tissues, cleaning milk, cleaning soap, foam or shower bath, deodorant, antiperspirant, hair shampoo, hair care agent, hair conditioner, hair colorant, hair styling agent and in this case preferably be present as an emulsion, lotion, milk, fluid, cream, hydro dispersion gel, balm, spray, alcoholic or aqueous/alcoholic solution, foam, powder, liquid soap, piece of soap, shampoo, roll-on, stick or make-up. In hair treatment agents, the use is preferably directed at the base of the hair or the scalp.

For cosmetic or therapeutic purposes, the above compound of group (i), (ii) and/or (iii) is applied to the skin and/or the hair in an adequate quantity.

Particular advantages are offered here by cosmetic, especially topic preparations which contain the above compound of group (i), (ii) and/or (iii) and additionally act as a sun protection means. Advantageously, these preparations contain at least one UVA filter and/or at least one UVB filter and/or at least one inorganic pigment. The cosmetic, especially topical preparations according to the present invention may be present here in various formulations such as are conventionally used for sun protection, for example a formulation selected from the group consisting of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

The present invention further relates to the use of an above compound of group (i), (ii) and/or (iii) for the production of an orally administered non-pharmaceutical preparation (also referred to as an orally administered non-pharmaceutical composition). This non-pharmaceutical preparation is administered orally, for example in the form of tablets (for example film tablets), coated tablets, capsules (for example gelatin capsules), granulates, juices, solutions, emulsions, micro emulsions, sprays or products which can be consumed orally in another form, or in the form of food, which, because
(i) a diastereomer or a mixture of two or more diastereomers of formula (I)

(I)

particularly a compound of formula (I) of group a) or d), or
(ii) a salt of a diastereomer or of a mixture of two or more diastereomers of formula (I), particularly a compound of formula (I) of group b) or e), or
(iii) a mixture of two or more salts of a diastereomer or of a mixture of two or more diastereomers of formula (I), particularly a compound of formula (I) of group c) or f) is contained therein may bring about "beauty from inside".

Furthermore the present invention relates to a method for the non-therapeutic
prevention, treatment or reduction of skin aging, especially skin wrinkles and/or
stimulation of the adipogenesis to increase the number of differentiated adipocytes and/or
inhibition of the lipolysis to alter the breakdown of stored lipids and thus increase the size of differentiated adipocytes, and/or
increase of the lipid content in the human subcutaneous adipose tissue, and/or
inhibition of the formation of free radicals and breakdown of free radicals comprising the following step:
application of an effective amount of
(i) a diastereomer or a mixture of two or more diastereomers of formula (I)

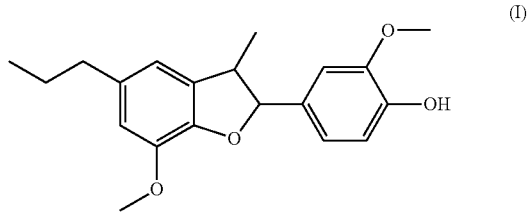 [SMILES: CCCc1cc(OC)c2c(c1)C(C)C(c1ccc(O)c(OC)c1)O2]

particularly a compound of formula (I) of group a) or d), or
(ii) a salt of a diastereomer or of a mixture of two or more diastereomers of formula (I), particularly a compound of formula (I) of group b) or e), or
(iii) a mixture of two or more salts of a diastereomer or of a mixture of two or more diastereomers of formula (I), particularly a compound of formula (I) of group c) or f)
or of a cosmetic, especially topical preparation as defined hereinabove to the skin or tissue in need thereof,
or application of effective amount of an orally administerable composition as defined hereinabove.

In the following the invention is further explained using examples. The examples serve to clarify the invention without limiting the scope of protection of the claims. Unless otherwise stated, all data relate to the weight.

EXAMPLE 1

Preparation of 2-Methoxy-4-(7-methoxy-3-methyl-5-propyl-2,3-dihydro-benzofuran-2-yl)-phenol (also known as Dihydrodehydrodiisoeugenol)

1a): Preliminary Stage:
Obtaining 2-Methoxy-4-(7-methoxy-3-methyl-5-propyl-2,3-dihydro-benzofuran-2-yl)-phenol (Compound of Formula (II), Also Known as Dehydrodiisoeugenol)

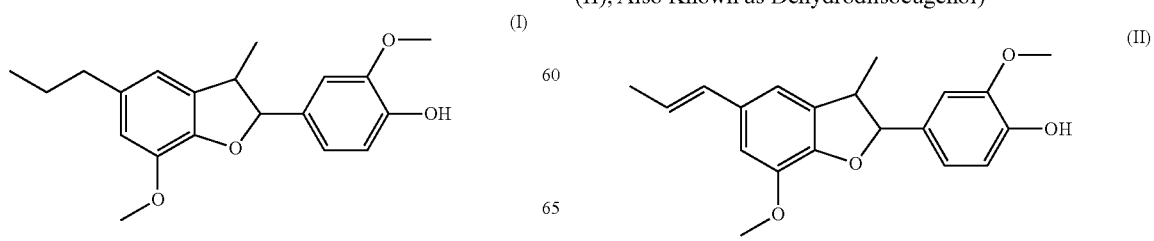

164 g of isoeugenol are dissolved in 700 g ethanol and cooled to 0-5° C. Then a solution of 276 g iron-(III)-chloride (×6H$_2$0) dissolved in 700 g water is added within 1 hour, at the abovementioned temperature. Agitation continues for a further approximately 6-8 hours at 0-5° C., wherein the product slowly precipitates as solid matter. Following filtration the deposit is washed with approximately 100 g of water, dissolved in methyl-tert.-butylether (MTBE) and washed with sodium carbonate. Following removal of the solvent with a rotary evaporator 48 g of product remain with a purity of 85%. Yield: 25% of theoretical.

1b) Final Stage:
Obtaining the Compound of Formula (I) by Hydrogenation of the Compound of Formula (II)

The 48 g compound of formula (II) obtainable as described under 1a) are dissolved in 400 g ethanol at 40° C., mixed with 0.5 g Pd/C (carbon-carried palladium catalyst) and hydrogenated at a hydrogen pressure of 10 bar and a temperature of 50° C. The hydrogen absorption is complete after approximately 3 hours. After the catalyst has been filtered off about half of the solvent is evaporated. The solution is cooled to 10° C. and crystallisation takes place. 38 g of product is obtained with a purity of >99%.

EXAMPLE 2

Quantification of Intracellular Lipids (In Vitro)

3T3-L1-cells (mouse embryonic fibroblast-like preadipocytes cell line) were propagated in Dulbecco's Modified Eagle Medium (DMEM), enriched with 10% newborn calf serum (CS) at 37° C. and 5% CO$_2$ and seeded in 48-well plates for lipid quantification. After reaching confluence at day −2 the differentiation was induced by changing medium at day 0 to DMEM with 10% fetal calf serum (FCS) containing a hormone mix (HM) of 1 µg/ml insulin, 0.25 µM dexamethasone (Dex) and 0.5 mM 3-isobutyl-1-methylxanthine (IBMX).

Compounds of interest such as compound of formula (I) are applied from day −2 (confluence of the cells) until day 2 using various concentrations. Medium is renewed every other day. At day 2, medium consisting of DMEM, 10% FCS and 1 µg/ml insulin is added. From day 4 on, only DMEM containing 10% FCS is used for further cultivation of cells. At day 10, quantification of the intracellular lipid droplets is performed by addition of the fluorescent dye Nile Red (9-diethylamino-5H-benzo[alpha]phenoxazine-5-one) for 20 minutes at 37° C. and 5% CO$_2$. Fluorescence (RFU) is detected with excitation at 485 nm and emission at 535 nm.

Stimulation of the adipogenesis in the presence of the compounds of interest is calculated according to the following equation:

$$\text{Stimulation of adipogeneis [\%]} = \left(\frac{RFU \text{ test substance} - RFU \text{ withoutcells}}{RFU \text{ control} - RFU \text{ withoutcells}} \times 100\right) - 100$$

wherein
RFU test substance=Relative Fluorescence Units of the wells with test substance and with cells
RFU control=Relative Fluorescence Units of the wells stimulated with hormone mix only.
RFU without cells=Relative Fluorescence Units of the wells containing Nile Red only, without cells.

TABLE 1

Stimulation of the adipogenesis of the individual substances (averages from at least 2 independent experiments)

| Compound | Stimulation of adipogenesis |
| --- | --- |
| 0.01 µM compound of formula (I) | 18 |
| 0.1 µM compound of formula (I) | 30 |
| 0.25 µM compound of formula (I) | 35 |
| 0.5 µM compound of formula (I) | 38 |
| 0.75 µM compound of formula (I) | 48 |
| 1 µM compound of formula (I) | 49 |
| 2.5 µM compound of formula (I) | 48 |
| 5 µM compound of formula (I) | 37 |
| 10 µM compound of formula (I) | 22 |
| 10 µM sarsasapogenin | 27 |
| 20 µM sarsasapogenin | 17 |

EXAMPLE 3

Real Time-PCR

3T3-L1-cells (mouse embryonic fibroblast-like preadipocytes cell line) were propagated in Dulbecco's Modified Eagle Medium (DMEM), enriched with 10% newborn calf serum (CS) at 37° C. and 5% CO$_2$ and seeded in 12-well plates for gene expression analysis. After reaching confluence at day −2, the differentiation was induced by changing medium at day 0 to DMEM with 10% fetal calf serum (FCS) containing a hormone mix (HM) of 1 µg/ml insulin, 0.25 µM dexamethasone (Dex) and 0.5 mM 3-isobutyl-1-methylxanthine (IBMX). Compounds of interest such as compound of formula (I) are applied from day −2 (confluence of the cells) until day 2 using various concentrations. Medium is renewed every other day. At day 2, medium consisting of DMEM, 10% FCS and 1 µg/ml insulin is added. From day 4 on, only DMEM containing 10% FCS is used for further cultivation of cells. For determination of gene expression samples are harvested during the differentiation process from day 2 to day 10.

Total RNA from cell culture samples was isolated using RNeasy Total RNA Kits (Qiagen, Hilden; Germany). The RNA concentration and purity was determined photometrically using 260/280 ratios (Biophotometer, Eppendorf, Hamburg, Germany). Aliquots of total RNA (100 ng) were applied for cDNA-Synthesis using Superscript™III First-Strand synthesis system for the reverse transcription step with random healers (Invitrogen, Karlsruhe, Germany). For each gene, a specific primer pair was designed by Primer Express™ 2.0 software (Applied Biosystems, Darmstadt, Germany) based on the published cDNA sequence. At least three independent experiments were performed with 2 determinations each and the mean value of these was calculated. The PCR reactions were carried out on an Opticon 1 (MJ Research, Waltham, Mass., USA) using SYBR Green® PCR Master Mix (Applied Biosystems, Darmstadt, Germany). Each sample was analyzed in duplicate employing the universal protocol over 46 cycles. In detail, 10 minutes 94° C. activation of hot start taw polymerase, 20 seconds 95° C. penetration, 20 seconds 55° C. annealing, 30 seconds 72° C. extension. For comparison of relative expression in real time PCR control cells stimulated with hormone mix alone and cells treated with hormone mix and the compound of interest the 2-ΔΔC(t) method was used (Livak and Schmittgen, Methods 2001, 25, 402-408). Results are given as fold induction compared to the hormone mix stimulation (set equal to one).

As markers of the differentiation process, differentiation specific adipocyte transcription factors such as the peroxisome proliferator-activated receptor γ2 (PPARγ2), and CCAAT enhancer binding protein α (C/EBPα) are studied. Moreover, fatty acid binding protein 4 (FABP4), and adiponectin are measured. Preadipocyte factor 1 (Pref1) maintains the undifferentiated state of preadipocytes and serves as a negative control of the differentiation. For each gene a specific PCR primer pair is created: 18S rRNA 5'-GTAAC-CCGTTGAACCCCATT-3'/5'-CCATCCAATCGGTAG-TAGCG-3' (Raynal et al, FEBS Lett 1984, 167, 263-268), PPARγ2 5'-CTGCTCA-AGTATGGTGTCCATGA-3'/5'-CT-GAGA TGAGGACTCCATCTTTATTCA-3' (Zhu et al, Proc Natl Acad Sci USA 1995, 92, 7921-7925), C/EBPα 5'-CG-CAAG-AGCCGAGATAAAGC-3'/5'-CGGTCATT-GT-CACTGGTCAACT-3' (Cao et al, Genes Dev 1991, 5, 1538-1552), FABP4 5'-GCGTGGAATTCG-ATGAAATCA-3'/5'-CCCGCCATCTAGGG-TTATGA-3' (Cook et al, Proc Natl Acad Sci USA 1988, 85, 2949-2953), adiponectin 5'-CGG-GACTCTACTACTTC-TCTTACCACAT-3'/5'-AGAACG-GCCTTGT-CCTCCTTG-3' (Hue et al, J Biol Chem 1996, 271, 10697-10703), Pref1 5'-CGGCCACAGCACC-TATGG-3'/5'-ACATTGTCAGCCTCGCA-GAA-3' (Smas and Sul, Cell 1993, 73, 725-734).

TABLE 2

Stimulation of the expression of various differentiation markers by compound of formula (I) (averages from at least 2 independent experiments)

| Differentiation marker | Stimulation of expression at day 2 | |
|---|---|---|
| | 1 μM compound of formula (I) | 10 μM compound of formula (I) |
| PPARγ2 | 1.0 | 1.5 |
| Adiponectin | 1.4 | 2.2 |
| C/EBPα | 1.1 | 2.2 |
| FABP4 | 2.1 | 3.3 |

TABLE 3

Inhibition of the expression of the preadipocytes marker Pref-1 by compound of formula (I) (averages from at least 2 independent experiments)

| | Inhibition of expression at day 2 | |
|---|---|---|
| | 1 μM compound of formula (I) | 10 μM compound of formula (I) |
| Pref-1 | 0.3 | 0.7 |

EXAMPLE 4

Lipolysis Assay (In Vitro)

3T3-L1-cells (mouse embryonic fibroblast-like preadipocytes cell line) were propagated in Dulbecco's Modified Eagle Medium (DMEM), enriched with 10% newborn calf serum (CS) at 37° C. and 5% $CO_2$ and seeded in 48-well plates for lipolysis. After reaching confluence at day −2 the differentiation was induced by changing medium at day 0 to DMEM with 10% fetal calf serum (FCS) containing a hormone mix (HM) of 1 μg/ml insulin, 0.25 μM dexamethasone (Dex) and 0.5 mM 3-isobutyl-1-methylxanthine (IBMX). Medium is renewed every other day. At day 2, medium consisting of DMEM, 10% FCS and 1 μg/ml insulin is added. From day 4 on, only DMEM containing 10% FCS is used for further cultivation of cells. For determination of lipolysis, compounds of interest are added at day 10 for 20 hours mixed with bovine serum albumin (BSA). If lipolysis occurs, cells secrete glycerol into the supernatant. Therefore, supernatants are harvested and determination of lipolysis is performed by using a free glycerol reagent. The quantification of the free glycerol is carried out on the basis of an enzymatic method with a free glycerol reagent.

The lipolysis in the presence of the test substances is calculated according to the following equation:

$$\text{Lipolysis } [\%] = \frac{A \text{ test substance} - A \text{ control without cells}}{A \text{ control} - A \text{ control without cells}}$$

wherein

A test substance=absorption of the wells with test substance and with cells

A control=absorption of the wells without test substance, but with cells

A control without cells=absorption of the wells without test substance and without cells

TABLE 4

Relative lipolysis compared to basal lipolysis by compound of formula (I) (averages from at least 2 independent experiments)

| | | Significance versus Basal Lipolysis (paired t-test) |
|---|---|---|
| Basal Lipolysis | 100% ± 2.1 | — |
| 1 μM compound of formula (I) | 85% ± 1.6 | ** |
| 10 μM compound of formula (I) | 85% ± 1.5 | ** |
| 10 μM Sarsapogenin | 99% ± 3.3 | — |
| 20 μM Sarsapogenin | 106% ± 3.5 | — |

EXAMPLE 5

COX-2-Assay (In Vitro)

Cyclooxygenase-2 (COX-2) in the presence of test substance is mixed with the fluorometric substrate 10-acetyl-3,7-dihydroxyphenoxanin (ADHP) and Heme. The reaction is started by addition of the substrate arachidonic acid.

COX-2 converts the arachidonic acid into the prostaglandin endoperoxide G2 (PGG2). PGG2 is reduced to the corresponding alcohol PGH2. During this reaction ADHP results in fluorescent resorufin. Resorufin is quantified at an extinction wavelength of 535 nm and an emission wavelength of 590 nm.

$$\text{Inhibition of } COX-2[\%] = 100 - \left( \frac{\text{Resorufin test substance} - \text{Resorufin control without } COX-2}{\text{Resorufin control} - \text{Resorufin control without } COX-2} \times 100 \right)$$

where

Resorufin test substance=Resorufin concentration of the wells with test substance and with COX-2

Resorufin control=Resorufin concentration of the wells without test substance, but with COX-2

Resorufin control without COX-2=Resorufin concentration of the wells without test substance and without COX-2

From the inhibition of the COX-2[%] in a series of dilutions of tested samples the IC50 is calculated. This is the concentration at which the activity of the COX-2 is inhibited by 50%.

As an average of at least 2 independent experiments the IC50 calculated from the inhibition of COX-2 is 12.3 ppm of compound of formula (I).

EXAMPLE 6

ABTS-Assay (In Vitro)

With the help of the ABTS-assay the anti-oxidative capacity of test substances is measured. 2,2'-azino bis-(3-ethylbenzothiazoline 6-sulfonic acid) (ABTS) is transformed by potassium persulfate into the blue-green radical cation ABTS•+. Through the addition of antioxidants (test substance) the radical cations are reduced and discoloration takes place, which is determined photometrically at 734 nm.

$$\text{Inhibition } [\%] = 100 - \left(\frac{A \text{ test substance}}{A \text{ control}} \times 100\right)$$

A test substance=absorption of the wells with test substance
A control=absorption of the wells without test substance From the inhibition of the radical formation [%] in a series of dilutions of tested samples the IC50 is calculated. This is the concentration at which the radical formation is inhibited by 50%.

As an average of at least 2 independent experiments the IC50 calculated from the inhibition of radical formation is 11.0 ppm of compound of formula (I).

FORMULATION EXAMPLES

Examples 1-9

Skin Care

1=Sun Protection Gel (SPF 6)
2=Sun Protection Lotion SPF 24 (UVA/UVB Balance)
3=Tinted Anti Aging Balm, SPF 15
4=Eye Contour Emulsion, SPF 15
5=Skin Soothing Night Cream O/W
6=Anti Wrinkle Night Cream W/O
7=Anti Wrinkle Ampoule
8=Anti Wrinkle Gel
9=Body Oil

| RAW MATERIAL NAME | INCI | WEIGHT % | | | | | | | | |
|---|---|---|---|---|---|---|---|---|---|---|
| | | 1 | 2 | 3 | 4 | 5 | 6 | 7 | 8 | 9 |
| Compound of formula (I) | | 0.1 | 0.02 | 0.01 | 0.05 | 0.1 | 0.7 | 0.02 | 0.02 | 0.2 |
| (−) alpha Bisabolol nat. | Bisabolol | | 0.1 | | 0.2 | | | | | |
| Abil 350 | Dimethicone | | | | 2 | | | | | |
| Actipone ® Laminaria SaccharinaGW | Glycerin, Water (Aqua), Laminaria Saccharina Extract | | | | | | 1 | | | |
| Aloe Vera Gel Conc.10:1 | Aloe Barbadensis Leaf Juice | | | | 1 | | | | | |
| Aluminium Stearate | Aluminium Stearate | | | | | | | | 1.2 | |
| Amaze XT | Dehydroxanthan Gum | 1.4 | | | | | | | | |
| Avocado Oil | Persea Gratissima (Avocado) Oil | | | | | | | | | 2 |
| Betulin 90% (1079) | Betulin | | | | | 0.15 | | | | |
| Biotive ® L-Arginine | Arginine | 3.2 | 0.5 | 0.6 | 0.9 | | | | | |
| Biotive ® Troxerutin | Troxerutin | | | 0.5 | 0.5 | | | | | |
| Carbopol ETD 2020 | Acrylates/C10-30 Alkyl Acrylate Crosspolymer | 0.2 | | | | | | | 0.7 | |
| Carbopol ETD 2050 | Carbomer | | | | 0.2 | | 0.2 | | | |
| Carbopol Ultrez-21 | Acrylates/C10-30 Alkyl Acrylate Crosspolymer | | | | | 0.5 | | | | |
| Corapan TQ | Diethylhexyl 2,6 Naphtalate | | | | | | 3 | | | |
| Cutina GMS V | Glyceryl Stearate | | | | | | 2 | | | |
| Cutina PES | Pentaerythrityl Distearate | | | | | 2 | | | | |
| Dermacryl AQF | Acrylates Copolymer | | | 2 | | | | | | |

-continued

| RAW MATERIAL NAME | INCI | 1 | 2 | 3 | 4 | 5 | 6 | 7 | 8 | 9 |
|---|---|---|---|---|---|---|---|---|---|---|
| Dipropylene Glycol | Dipropylene Glycol | | | | | | | | 7 | |
| Dow Corning 193 surfactant | PEG-12 Dimethicone | 1 | | | | | | | 2 | |
| Dow Corning 246 fluid | Cyclohexasiloxane | | | 3 | | 1 | | | | |
| D-Panthenol 75 L | Panthenol | | | | | | | 1 | | |
| Dracorin ® CE | Glyceryl Stearate/Citrate | | | | | 3 | | | | |
| Dracorin ® GOC | Glyceryl Oleate Citrate, Caprylic Capric Triglyceride | | | | 1.5 | | | | | |
| Drago-Beta-Glucan | Water (Aqua), Butylene Glycol, Glycerin, *Avena Sativa* (Oat) Kernel Extract | | | | | | | | 1 | |
| DragoCalm ® | Water, Glycerin, *Avena Sativa* (Oat Kernel Extract) | | | | | | | 1 | | |
| Dragocide ® Liquid | Phenoxyethanol, Methylparaben, Ethylparaben, Butylparaben, Propylparaben, Isobutylparaben | | | | | 0.8 | 0.8 | | | |
| Dragoderm ® | Glycerin, *Triticum Vulgare* (Wheat) Gluten, Water (Aqua) | | | | | 2 | | | | |
| Dragosan W/O P | Sorbitan Isostearate, Hydrogenated Castor Oil, Ceresin, Beeswax (*Cera Alba*) | | | | | | 8 | | | |
| Dragosantol ® 100 | Bisabolol | | | 0.1 | | | 0.2 | | | |
| Dragosine ® | Carnosine | 0.2 | | | | | | 0.2 | 0.2 | |
| Dragoxat ® 89 | Ethylhexyl Isononanoate | | 2 | 5 | | 4 | 7 | | | 10 |
| EDTA B | Tetrasodium EDTA | | | | | | | | 0.2 | |
| EDTA BD | Disodium EDTA | | 0.1 | 0.1 | 0.1 | | | | | |
| Emulsiphos ® | Potassium Cetyl Phosphate, Hydrogenated Palm Glycerides | | 2 | 2 | | | | | | |
| Ethanol 96% | Ethanol | 10 | | | | | | | | |
| Extrapone ® *Ginkgo Biloba* | Propylene Glycol, Water (Aqua), *Ginkgo Biloba* Leaf Extract, Glucose, Lactic Acid | | | | | 1 | | | | |
| Food Color Brown E172 + E171 Powder | Color | | | | 2 | | | | | |
| Fragrance | Parfum | 0.1 | 0.2 | 0.3 | | 0.4 | 0.3 | 0.1 | 0.1 | 0.5 |
| Frescolat ® MGA | Menthone Glycerin Acetal | | | | | | | 0.1 | | |

-continued

| RAW MATERIAL NAME | INCI | WEIGHT % | | | | | | | | |
|---|---|---|---|---|---|---|---|---|---|---|
| | | 1 | 2 | 3 | 4 | 5 | 6 | 7 | 8 | 9 |
| Frescolat ® ML | Menthyl Lactate | | | 0.1 | | | | | | |
| Fruitapone ® Orange B | Propylene Glycol, Water (Aqua), Citric Acid, *Citrus Aurantium Dulcis* (Orange) Juice, Trideceth-9, Bisabolol | | | | | | | | 1 | |
| Glycerin 99.5% | Glycerin | 2.5 | 3 | | | 5 | 3 | | 4 | |
| Hydrolite ®-5 | Pentylene Glycol | 3 | 2 | | 5 | | | | 4.5 | |
| Hydroviton ®-24 | Water, Pentylene Glycol, Glycerin, Lactic Acid, Sodium Lactate, Serine, Urea, Sorbitol, Sodium Chloride, Allantoin | | | | | 1 | 1 | | | |
| Iso Adipat | Diisopropyl Adipate | | | | 1 | | | | | |
| Isodragol ® | Triisononanoin | | 2 | | | | | | | 13 |
| Jojoba Oil | *Simmondsia Chinensis* (Jojoba) Seed Oil | 1 | | | | | 2 | | | |
| Keltrol CG RD | Xanthan Gum | | 0.4 | 0.2 | 0.2 | 0.1 | | 0.05 | | |
| Lanette 16 | Cetyl Alcohol | | 1 | | | | | | | |
| Lanette O | Cetearyl Alcohol | | 0.5 | | | 3 | | | | |
| Lara Care A-200 | Galactoarabinan | | 0.3 | | | | | | | |
| Macadamia Nut Oil | *Macadamia Ternifolia* Seed Oil | | | | | | | | | 0.5 |
| Magnesium Sulfate | Magnesium Sulfate | | | | | | 0.7 | | | |
| Mineral Oil | Mineral Oil | | | | | | | 8 | | 49.65 |
| Neo Heliopan ® 303 | Octocrylene | | 10 | 4 | | | | | | |
| Neo Heliopan ® 357 | Butylmethoxydibenzoylmethane | | 3 | 2 | 3 | | | | | |
| Neo Heliopan ® AP | Disodium Phenyl Dibenzimidazole Tetrasulfonate | 3 | | | | | | | | |
| Neo Heliopan ® AP, 15% sol., neutralized with Biotive ® L-Arginine | Aqua, Disodium Phenyl Dibenzimidazole Tetrasulfonate, Arginin | | | 6.7 | 6.7 | | | | | |
| Neo Heliopan ® E 1000 | Isoamyl p.Methoxycinnamate | | 1 | | | | | | | |
| Neo Heliopan ® HMS | Homosalate | | | 5 | | 5 | | | | |
| Neo Heliopan ® Hydro, 20% sol., neutralized with Biotive ® L-Arginine | Aqua, Phenylbenzimidazole Sulphonic Acid, Arginin | | 10 | 10 | 10 | | | | | |
| Neo Heliopan ® MBC | 4-Methylbenzylidene Camphor | 1 | | | | | | | | |
| Neo Heliopan ® OS | Ethylhexyl Salicylate | | | 3 | 5 | | | | | |
| Neutral Oil | Caprylic/Capric Triglyceride | | | | | | 6 | | | |

-continued

| RAW MATERIAL NAME | INCI | \multicolumn{9}{c}{WEIGHT %} |
|---|---|---|---|---|---|---|---|---|---|---|
| | | 1 | 2 | 3 | 4 | 5 | 6 | 7 | 8 | 9 |
| Ozokerite Wax 2389 | Ozokerite | | | | | | 2 | | | |
| PCL-Liquid 100 | Cetearyl Ethylhexanoate | | | 2 | | 4 | 5 | | | 21 |
| PCL-Solid | Stearyl Heptanoate, Stearyl Caprylate | | | | | 3 | | | | |
| Phytoconcentrole ® Shea Butter | *Glycine Soja* (Soybean) Oil, *Butyrospermum Parkii* (Shea Butter) | | | | | | | | | 0.5 |
| Silcare Silicone 41M65 | Stearyl Dimethicone | | 1 | | | | | | | |
| Sodium Chloride | Sodium Chloride | | | | | | | | | |
| Sodium Hydroxide 10% sol. | Sodium Hydroxide | | | | | 0.9 | | | 3.3 | |
| Solubilizer | PEG-40Hydrogenated Castor Oil, Trideceth-9, Propylene Glycol, Water (Aqua) | | | | | | | 1.5 | 0.8 | |
| SymCalmin ® | Pentylene Glycol, Butylene Glycol, Hydroxyphenyl Propamidobenzoic Acid | | | | | 1 | | | | |
| SymClariol ® | Decylene Glycol | | | | 0.5 | | | | | |
| SymDiol ® 68 | 1,2 Hexanediol, Caprylyl Glycol | 0.6 | | | | | | 1 | 0.5 | 1 |
| SymGlucan ® | Water (Aqua) Glycerin, Beta Glucan | | | 2 | | 2 | 1 | 5 | | |
| SymHelios ® 1031 | Benzylidene Dimethoxydimethylindanone | | | 0.5 | 0.5 | | | | | |
| SymMatrix ® | Maltodextrin, *Rubus Fruticosus* (Blackberry) Leaf Extract | | | | | | 0.5 | | | |
| SymMollient ® L | Neopentyl Glycol Diisononanoate | | | | | 2 | | | | |
| SymMollient ® S | Cetearyl Nonanoate | | | | | 1 | | | | |
| SymMollient ® W/S | Trideceth-9, PEG-5 Isononanoate | | | | | | | | 2 | |
| SymRelief ® | Bisabolol, *Zingiber Officinale* (Ginger) Root Extract | | | 0.1 | | 0.2 | | | 0.1 | 0.1 |
| SymRepair ® | Hexyldecanol, Bisabolol, Cetylhydroxyproline Palmitamide, Stearic Acid, *Brassica Campestris* (Rapeseed Sterols) | | | | 1 | | 3 | | | 1 |
| SymSitive ® 1609 | Pentylene Glycol, 4-t-Butylcyclohexanol | | | | | 0.5 | | | | |

-continued

| RAW MATERIAL NAME | INCI | WEIGHT % | | | | | | | | |
|---|---|---|---|---|---|---|---|---|---|---|
| | | 1 | 2 | 3 | 4 | 5 | 6 | 7 | 8 | 9 |
| SymVital ® | Aloe Barbadensis Leaf Juice Powder, Magnesium Ascorbyl Phosphate, Rubus Idaeus (Raspberry) Leaf Extract | 0.5 | | | | | | 0.1 | 0.5 | |
| Tapioca Pure | Tapioca Starch | | 5 | | | | | | | |
| Tegosoft PC41 | Polyglyceryl-4 Caprate | | | | | | | | 0.5 | |
| Tegosoft TN | C12-15 Alkyl Benzoate | | | | | 5 | | | | |
| Vitamin A Palmitate | Retinyl Palmitate | | | | | | | | | 0.05 |
| Vitamin E acetat | Tocopherol Acetate | | 0.5 | 0.5 | 0.5 | | 0.2 | | 0.5 | |
| Water, demin. | Water (Aqua) | ad 100 | ad 100 | ad 100 | ad 100 | ad 100 | ad 100 | ad 100 | ad 100 | |

EXAMPLES 10-18

Hair Care

10=Hair tonic
11=After sun shampoo
12=Hair conditioner with UVB/UVA protection
13=Liquid hair leave-on, pump-foam
14=Hair styling gel
15=Hair setting foam
16=Mascara
17=Anti-dandruff shampoo
18=Shampoo

| RAW MATERIAL NAME (SUPPLIER) | INCI | WEIGHT % | | | | | | | | |
|---|---|---|---|---|---|---|---|---|---|---|
| | | 10 | 11 | 12 | 13 | 14 | 15 | 16 | 17 | 18 |
| Compound of formula (I) | | 0.05 | 0.2 | 0.1 | 0.02 | 0.05 | 0.01 | 0.01 | 0.2 | 0.2 |
| Abil B 9950 (Evonic Goldschmidt) | Dimethicone Propyl Pg-Betaine | | | | 0.2 | | | | | |
| Abil-Quat 3272 (Evonic Goldschmidt) | Quaternium-80 | | | | 0.5 | | | | | |
| Actipone AlphaPulp (Symrise) | Water (Aqua), Butylene Glycol, Malic Acid, Actinidia Chinensis (Kiwi) Fruit Juice, Citrus Aurantium Dulcis (Orange) Juice, Citrus Paradisi (Grapefruit) Juice, Pyrus Malus (Apple) Juice, Trideceth-9, Prunus Amygdalus Dulcis (Sweet Almond) Seed Extract | | | | 0.75 | | | | | |
| Aloe Vera Gel Concentrate 10/1 (Symrise) | Water (Aqua), Aloe Barbadensis Leaf Juice | | | 0.5 | | | | | | |
| -(-Alpha-)-Bisabolol, natural (Symrise) | Bisabolol | | | | | | | | 0.1 | |
| Aminexil | Diaminopyrimidine Oxide | 0.3 | | | | | | | | |
| Antil 141 Liquid (Evonic Goldschmidt) | Propylene Glycol, PEG-55 Propylene Glycol Distearate | | | 1.0 | | | | | | |

-continued

| RAW MATERIAL NAME (SUPPLIER) | INCI | WEIGHT % | | | | | | | | |
|---|---|---|---|---|---|---|---|---|---|---|
| | | 10 | 11 | 12 | 13 | 14 | 15 | 16 | 17 | 18 |
| Antil 171 (Evonic Goldschmidt) | PEG-18 Glyceryl Oleate/Cocoate | | | | | | | | 2.0 | |
| Carbopol ETD 2001 (Noveon) | Carbomer | | | | | 0.7 | | | | |
| Celquat L-200 (National Starch & Chemical) | Polyquaternium-4 | | | | 1.0 | | | | | |
| CeramideBio (Symrise) | N-(1-Hexadecanoyl)-4-hydroxy-L-prolin-(1-hexadecyl-ester | | 0.2 | | | | | | | |
| Citric Acid 10% solution | Citric Acid | | | | 1.3 | 1.6 | | | | q.s. |
| Colour (Symrise) | Colour | | | | | | | | 0.2 | |
| Crinipan AD (Symrise) | Climbazole | | | | | | | | 0.5 | |
| Crotein Q (Croda) | Hydroxypropyl Trimonium Hydrolyzed Collagen | | | 1.0 | | | | | | |
| Dehyquart A CA (Cognis) | Cetrimonium Chloride | 0.2 | 1.0 | | | 4.0 | | | | |
| Dehyquart SP (Cognis) | Quaternium-52 | | | 0.5 | | | | | | |
| Dehyton K (Cognis) | Cocamidopropyl Betaine | | 8.0 | | | | 0.5 | | | 2.0 |
| D-Panthenol 75L (DSM Nutritional) | Panthenol | 0.5 | 1.0 | | | 0.5 | | | | |
| Dow Corning 245 Fluid | Cyclopentasiloxane | | | | | | | 5.0 | | |
| Dow Corning 5225C Formulation Aid | Cyclopentasiloxane, PEG/PPG-18/18 Dimethicone | | | | | | | 1.0 | | |
| Dracorin GMS (Symrise) | Glyceryl Stearate | | | | | | | 2.0 | | |
| Dragocide Liquid (Symrise) | Phenoxyethanol, Methyl-, Ethyl-, Butyl-, Propyl-, Isobutylparaben | | 0.8 | 0.5 | | 0.5 | | | 0.7 | 0.5 |
| Dragocolor Blue (Symrise) | Basic Blue 99 | | | | | | | | | 0.02 |
| Dragocolor Brown (Symrise) | Basic Brown 17 | | | | | | | | | 0.1 |
| Dragocolor Mahagony (Symrise) | Basic Brown 16 | | | | | | | | | 0.1 |
| Dragoderm (Symrise) | Glycerin, *Triticum Vulgare* (Wheat) Gluten, Water (Aqua) | | | 1.0 | | | | | | |
| Edeta BD (BASF) | Disodium EDTA | | | | | | | 0.05 | | |
| Emulgin B2 (Cognis) | Ceteareth-20 | | | | 0.7 | | | | | |
| Ethanol 96% | Ethanol | 48.0 | | | 3.0 | 5.0 | 13.0 | | 3.0 | |
| Euperlan PK 771 (Cognis) | Glycol Distearate, Sodium Laureth Sulfate, Cocamide MEA, Laureth-10 | | | | | | | | 3.0 | |
| Euperlan PK 900 BENZ-W (Cognis) | PEG-3 Distearate | | | | | | | | | 2.0 |
| Euperlan PK 4000 (Cognis) | Glycol Distearate, Laureth-4, Cocoamidopropyl Betaine | | | 2.5 | | | | | | |
| Ewacera 12 (H. Erhard Wagner) | Bees Wax | | | | | | | 10.0 | | |
| Ewacera 34 (H. Erhard Wagner) | Carnauba Wax | | | | | | | 4.0 | | |

-continued

| RAW MATERIAL NAME (SUPPLIER) | INCI | WEIGHT % | | | | | | | | |
|---|---|---|---|---|---|---|---|---|---|---|
| | | 10 | 11 | 12 | 13 | 14 | 15 | 16 | 17 | 18 |
| Extrapone Camomile (Symrise) | Water (Aqua), Propylene Glycol, Butylene Glycol, *Chamomilla Recutita* (Matricaria) Flower Extract, Glucose, Bisabolol | | | | | | | | 0.5 | |
| Extrapone Green Tea GW (Symrise) | Glycerin, Water (Aqua), *Camellia Sinensis* Leaf Extract | | | | | | | | 0.3 | |
| Extrapone Hop GW (Symrise) | Glycerin, Water (Aqua), *Humulus Lupulus* (Hops) Cone Extract, Glucose | 0.4 | | | | | | | | |
| Extrapone Lemongrass (Symrise) | Propylene Glycol, Water (Aqua), PEG-40 Hydrogenated Castor Oil, Trideceth-9, Cymbopogon Citratus Leaf Oil, Lactic Acid | 0.4 | | | | | | | | |
| Extrapone Rosemary GW (Symrise) | Glycerin, Water (Aqua), *Rosmarinus officinalis* (Rosemary) Leaf Extract | | 0.3 | | | | | | | |
| Fragrance (Symrise) | Fragrance | 0.5 | 0.3 | 0.4 | 0.2 | 0.4 | 0.5 | | 0.5 | 0.4 |
| Frescolat ML (Symrise) | Menthyl Lactate | 0.5 | | | | 0.8 | | | 0.5 | |
| Glycerin, 99.5% | Glycerin | | | | | 10.0 | | | | |
| Hydrolite-5 (Symrise) | Pentylene Glycol | | | | 0.5 | | | | | |
| Keltrol T (Calgon) | Xanthan Gum | | | | | | | 0.15 | | |
| Lanette 18 (Cognis) | Stearyl Alcohol | | | | | | | 2.0 | | |
| Lanette O (Cognis) | Cetearyl Alcohol | | | 2.5 | | | | | | |
| Luviskol K 30 (BASF) | PVP | | | | 2.0 | | | | | |
| Luviskol K 30 Powder (BASF) | PVP/Polyvinylpyrrolidone | | | | | 3.0 | | 4.0 | | |
| Luviskol VA 64 Powder (BASF) | PVP/VA Copolymer | | | | | | | 4.0 | | |
| MBD 210 20% Dispersion | Carbon Black, Water (Aqua) | | | | | | | 5.0 | | |
| Merquat 550 (Ondeo) | Polyquaterinium-7 | | 1.0 | | | | | | | |
| Mulsifan RT 203/80 (Z&S) | C12-15 Pareth-12 | | | | | 4.0 | | | | |
| Neo Heliopan 357 (Symrise) | Butyl Methoxydibenzoyl methane | | | 0.5 | | | | | | |
| Neo Heliopan BB (Symrise) | Benzophenone-3 | 0.1 | 0.2 | | | | | | 0.3 | |
| Neo Heliopan E 1000 (Symrise) | Isoamyl-p-methoxy-cinnamate | | | 2.0 | | | | | | |
| Neo-PCL Water soluble N (Symrise) | Trideceth-9, PEG-5 Ethylhexanoate, Water (Aqua) | | | | | 1.0 | | | | |
| Neutrol TE (BASF) | Tetrahydroxypropyl Ethylendiamine | | | | | 1.4 | | | | |
| Niacinamide | Niacinamide | 0.2 | | | | | | | | |
| Permethyl 104A (Cesham) | Polyisobutene C68 | | | | | | | 1.0 | | |
| Plantacare 1200 UP (Cognis) | Lauryl glucoside | | | | | | | | | 10.0 |

-continued

| RAW MATERIAL NAME (SUPPLIER) | INCI | WEIGHT % | | | | | | | | |
|---|---|---|---|---|---|---|---|---|---|---|
| | | 10 | 11 | 12 | 13 | 14 | 15 | 16 | 17 | 18 |
| Polymer JR 400 (Nordmann, Rassmann) | Polyquaternium-10 | | | | | | | | 0.2 | |
| Potassium Sorbate | Potassium Sorbate | | | | 0.2 | | | | | |
| Prestige Sparkling Pure Gold (Eckart) | Mica, Titanium Dioxide, Iron Oxides | | | | | | | 3.0 | | |
| Propane Butane 4,2 Bar | Propane-Butane | | | | | | 10.0 | | | |
| 1,2-Propylenglycol | Propylene Glycol | | | | | | | 2.0 | | |
| Rose CL forte (Symrise) | Water (Aqua), Glycerin, PEG-40 Hydrogenated Castor Oil, Rosa Damascena Flower Oil | | 0.5 | | | | | | | |
| Sodium Benzoate | Sodium Benzoate | | | | 0.5 | | | | | |
| Sodium Chloride | Sodium Chloride | | 0.5 | | | | | | 2.0 | |
| Sodium Hydroxide, 10% sol. | Sodium Hydroxide | | 0.1 | | | | | | | |
| Solubilizer (Symrise) | PEG-40 Hydrogenated Castor Oil, Trideceth-9, Water (Aqua) | 1.0 | | | | | | | | |
| Stearic Acid (Cognis) | Stearic Acid | | | | | | | 2.0 | | |
| Tego Betain 810 (Evonic Goldschmidt) | Capryl/Capramido propyl Betaine | | | | 0.5 | | | | | |
| Texapon K 14 S Special (Cognis) | Sodium Myreth Sulfate | | | | | | | | 12.0 | |
| Texapon N 70 (Cognis) | Sodium Laureth Sulfate | | 10.0 | | | | | | 12.0 | |
| Triethanolamine | Triethanolamine | | | | | | | 0.5 | | |
| Veegum HV | Magnesium Aluminium Silicate | | | | | | | 0.55 | | |
| Water, demineralized | Wasser (Aqua) | Ad 100 | Ad 100 | Ad 100 | Ad 100 | Ad 100 | Ad 100 | Ad 100 | Ad 100 | Ad 100 |

The invention claimed is:

1. A method for treating lipoatrophy comprising:
   (a) topically applying to skin of a patient in need thereof a cosmetic composition comprising:
      (i) an effective amount of a compound of formula (I), and/or a cosmetically acceptable salt thereof,

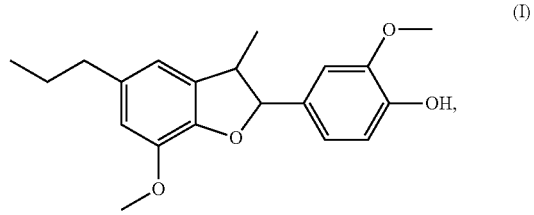 [SMILES: CCCc1cc(OC)c2c(c1)C(C)C(c1ccc(O)c(OC)c1)O2]

(I)

and
      (ii) a cosmetic carrier material; and
   (b) stimulating adipogeneesis to increase the number of differentiated adipocytes and/or inhibiting lipolysis to alter the breakdown of stored lipids to increase the size of differentiated adipocytes.

2. The method of claim 1, wherein the composition is an aqueous composition having a pH in the range of 5 to 9.

3. The method of claim 1, wherein the composition is a composition selected from the group consisting of pump sprays, aerosol sprays, creams, ointments, tinctures, and lotions.

4. The method of claim 1, wherein cosmetic composition comprises:
   (1) 0.001 to 5.0 wt. % of a compound of formula (I), and/or a cosmetically acceptable salt thereof.

5. The method of claim 1, wherein cosmetic composition comprises:
   (i) 0.005 to 2.0 wt. % of a compound of formula (I), and/or a cosmetically acceptable salt thereof.

6. The method of claim 1, wherein cosmetic composition comprises:
   (i) 0.01 to 1.0 wt. % of a compound of formula (I), and/or a cosmetically acceptable salt thereof.

7. The method of claim 1, wherein cosmetic composition comprises:
   (i) 0.02 to 0.5 wt. % of a compound of formula (I), and/or a cosmetically acceptable salt thereof.

8. The method of claim 1, wherein the carrier material is a liquid carrier material selected from the group consisting of glycerol, 1,2-propylene glycol, 1,2-butylene glycol, 1,3-butylene glycol, 1,2-pentandiol, 1,2-hexandiol, 1,2-octandiol, 1,2-decandiol, ethanol, water and mixtures thereof.

9. The method of claim 1, wherein the carrier material is a solid carrier material selected from the group consisting of a starch, a dextrin, a maltodextrin, lactose, silicon dioxide, glucose, a modified cellulose, gum arabic, ghatti gum, traganth, karaya, carrageenan, pullulan, curdlan, xanthan gum, gellan gum, guar flour, carob bean flour, alginates, agar, pectin and inulin and mixtures thereof.

10. The method of claim 1, wherein the cosmetic composition is free of carnitine and carnosine.

11. A method for treating lipoatrophy comprising:
(a) topically applying to skin of a patient in need thereof a cosmetic composition comprising:
(i) 0.001 to 5.0 wt. % of a compound of formula (I), and/or a cosmetically acceptable salt thereof,

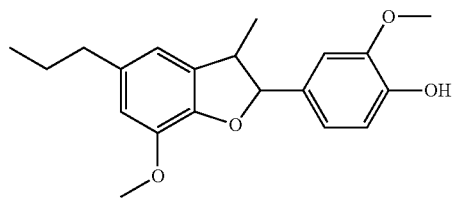

(I)

and
(ii) a cosmetic carrier material selected from the group consisting of glycerol, 1,2-propylene glycol, 1,2-butylene glycol, 1,3-butylene glycol, 1,2-pentandiol, 1,2-hexandiol, 1,2-octandiol, 1,2-decandiol, ethanol, water and mixtures thereof,
(b) stimulating adipogeneesis to increase the number of differentiated adipocytes and/or inhibiting lipolysis to alter the breakdown of stored lipids to increase the size of differentiated adipocytespreventing.

12. The method of claim 1, wherein the composition is a composition selected from the group consisting of pump sprays, aerosol sprays, creams, ointments, tinctures, and lotions.

13. The method of claim 11, wherein the cosmetic composition is free of carnitine and carnosine.

* * * * *

```
                        SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: Raynal et al, FEBS Lett 1984, 167, 263-268

<400> SEQUENCE: 1
gtaacccgtt gaacccatt                                                  20

<210> SEQ ID NO 2
<211> LENGTH: 20
<212> TYPE: DNA
<213> ORGANISM: artificial
<220> FEATURE:
<223> OTHER INFORMATION: Raynal et al, FEBS Lett 1984, 167, 263-268

<400> SEQUENCE: 2
ccatccaatc ggtagtagcg                                                 20

<210> SEQ ID NO 3
```

-continued

```
<211> LENGTH: 23
<212> TYPE: DNA
<213> ORGANISM: artificial
<220> FEATURE:
<223> OTHER INFORMATION: Zhu et al, Proc Natl Acad Sci USA 1995, 92,
      7921-7925

<400> SEQUENCE: 3
ctgctcaagt atggtgtcca tga                                            23

<210> SEQ ID NO 4
<211> LENGTH: 27
<212> TYPE: DNA
<213> ORGANISM: artificial
<220> FEATURE:
<223> OTHER INFORMATION: Zhu et al, Proc Natl Acad Sci USA 1995, 92,
      7921-7925

<400> SEQUENCE: 4
ctgagatgag gactccatct ttattca                                        27

<210> SEQ ID NO 5
<211> LENGTH: 20
<212> TYPE: DNA
<213> ORGANISM: artificial
<220> FEATURE:
<223> OTHER INFORMATION: Cao et al, Genes Dev 1991, 5, 1538-1552

<400> SEQUENCE: 5
cgcaagagcc gagataaagc                                                20

<210> SEQ ID NO 6
<211> LENGTH: 22
<212> TYPE: DNA
<213> ORGANISM: artificial
<220> FEATURE:
<223> OTHER INFORMATION: Cao et al, Genes Dev 1991, 5, 1538-1552

<400> SEQUENCE: 6
cggtcattgt cactggtcaa ct                                             22

<210> SEQ ID NO 7
<211> LENGTH: 21
<212> TYPE: DNA
<213> ORGANISM: artificial
<220> FEATURE:
<223> OTHER INFORMATION: Cook et al, Proc Natl Acad Sci USA 1988, 85,
      2949-2953

<400> SEQUENCE: 7
gcgtggaatt cgatgaaatc a                                              21

<210> SEQ ID NO 8
<211> LENGTH: 20
<212> TYPE: DNA
<213> ORGANISM: artificial
<220> FEATURE:
<223> OTHER INFORMATION: Cook et al, Proc Natl Acad Sci USA 1988, 85,
      2949-2953

<400> SEQUENCE: 8
cccgccatct agggttatga                                                20

<210> SEQ ID NO 9
<211> LENGTH: 28
<212> TYPE: DNA
<213> ORGANISM: artificial
```

```
<220> FEATURE:
<223> OTHER INFORMATION: Hue et al, J Biol Chem 1996, 271, 10697-10703

<400> SEQUENCE: 9
cgggactcta ctacttctct taccacat                                           28

<210> SEQ ID NO 10
<211> LENGTH: 21
<212> TYPE: DNA
<213> ORGANISM: artificial
<220> FEATURE:
<223> OTHER INFORMATION: Hue et al, J Biol Chem 1996, 271, 10697-10703

<400> SEQUENCE: 10
agaacggcct tgtcctcctt g                                                  21

<210> SEQ ID NO 11
<211> LENGTH: 18
<212> TYPE: DNA
<213> ORGANISM: artificial
<220> FEATURE:
<223> OTHER INFORMATION: Smas and Sul, Cell 1993, 73, 725-734

<400> SEQUENCE: 11
cggccacagc acctatgg                                                      18

<210> SEQ ID NO 12
<211> LENGTH: 20
<212> TYPE: DNA
<213> ORGANISM: artificial
<220> FEATURE:
<223> OTHER INFORMATION: Smas and Sul, Cell 1993, 73, 725-734

<400> SEQUENCE: 12
acattgtcag cctcgcagaa                                                    20
```